(12) United States Patent
Herweck et al.

(10) Patent No.: US 6,981,977 B2
(45) Date of Patent: Jan. 3, 2006

(54) BODY FLUID CARTRIDGE EXCHANGE PLATFORM DEVICE

(75) Inventors: Steve A. Herweck, Nashua, NH (US); Paul Martakos, Pelham, NH (US)

(73) Assignee: Atrium Medical Corporation, Hudson, NH (US)

( * ) Notice: Subject to any disclaimer, the term of this patent is extended or adjusted under 35 U.S.C. 154(b) by 78 days.

(21) Appl. No.: 10/045,544

(22) Filed: Oct. 26, 2001

(65) Prior Publication Data

US 2003/0083678 A1 May 1, 2003

(51) Int. Cl.
*A61B 17/08* (2006.01)

(52) U.S. Cl. ...................... 606/153; 604/175
(58) Field of Classification Search ............... 606/153, 606/155, 108, 109; 604/175, 29, 43, 93.01
See application file for complete search history.

(56) References Cited

U.S. PATENT DOCUMENTS

| 958,854 | A | | 5/1910 | Bunn |
|---|---|---|---|---|
| 3,416,532 | A | | 12/1968 | Grossman |
| 3,826,257 | A | * | 7/1974 | Buselmeier ................ 604/175 |
| 3,853,126 | A | * | 12/1974 | Schulte ................ 604/175 |
| 3,998,222 | A | * | 12/1976 | Shihata ................ 604/175 |
| 4,054,139 | A | | 10/1977 | Crossley |
| 4,326,516 | A | | 4/1982 | Schultz et al. |
| 4,346,703 | A | | 8/1982 | Dennehey et al. |
| 4,405,319 | A | | 9/1983 | Cosentino ................ 604/175 |
| 4,432,764 | A | | 2/1984 | Lopez |
| 4,440,207 | A | | 4/1984 | Genatempo et al. |
| 4,496,349 | A | | 1/1985 | Cosentino ................ 604/175 |
| 4,639,247 | A | | 1/1987 | Bokros ................ 604/175 |
| 4,648,391 | A | | 3/1987 | Ellis ................ 128/132 R |
| 4,654,033 | A | | 3/1987 | Lapeyre et al. ................ 604/175 |
| 4,684,367 | A | | 8/1987 | Schaffer et al. |
| 4,692,146 | A | | 9/1987 | Hilger |
| 4,767,410 | A | | 8/1988 | Moden et al. |
| 4,778,452 | A | | 10/1988 | Moden et al. |
| 4,781,695 | A | | 11/1988 | Dalton |
| 4,810,241 | A | | 3/1989 | Rogers |
| 4,822,341 | A | * | 4/1989 | Colone ................ 604/175 |
| 4,886,501 | A | | 12/1989 | Johnston et al. |
| 4,915,690 | A | | 4/1990 | Cone et al. |

(Continued)

FOREIGN PATENT DOCUMENTS

JP 7-255854 10/1995

(Continued)

OTHER PUBLICATIONS

Vasca, Inc. "Introducing LifeSite: The First Subcutaneous Hemodialysis Access System" Platform Access Device PAD And Accessories Jan. 30, 2001.

*Primary Examiner*—Julian W. Woo
(74) *Attorney, Agent, or Firm*—Lahive & Cockfield, LLP

(57) ABSTRACT

An apparatus for establishing a re-usable, recurring, mechanical connection to an organ within a patient is provided. A body fluid cartridge exchange platform device includes a hollow cartridge platform housing with a first end having an opening. The platform housing can additionally have a second end with a second opening. The first opening and the second opening facilitate insertion of an exchange cartridge insert that sealably engages the housing. The first opening and the second opening additionally facilitate removal of the exchange cartridge insert. The exchange cartridge insert can facilitate a flow path between a first leg and a second leg of the platform housing, and can facilitate a flow path between the platform housing and an external location for medical procedure or drug delivery purposes.

43 Claims, 9 Drawing Sheets

U.S. PATENT DOCUMENTS

| | | |
|---|---|---|
| 5,030,213 A | 7/1991 | Rumberger et al. |
| 5,147,483 A | 9/1992 | Melsky et al. |
| 5,167,638 A | 12/1992 | Felix et al. |
| 5,190,534 A | 3/1993 | Kendell |
| 5,226,879 A | 7/1993 | Ensminger et al. |
| 5,263,930 A | 11/1993 | Ensminger |
| 5,281,199 A | 1/1994 | Ensminger et al. |
| 5,281,205 A | 1/1994 | McPherson |
| 5,350,360 A | 9/1994 | Ensminger et al. |
| 5,375,589 A | 12/1994 | Bhatta |
| 5,399,168 A | 3/1995 | Wadsworth, Jr. et al. |
| 5,417,656 A | 5/1995 | Ensminger et al. |
| 5,474,526 A | 12/1995 | Danielson et al. ............. 604/4 |
| 5,501,426 A | 3/1996 | Atkinson et al. |
| 5,512,048 A | 4/1996 | Slettenmark |
| 5,527,277 A | 6/1996 | Ensminger et al. |
| 5,533,708 A | 7/1996 | Atkinson et al. |
| 5,562,618 A | 10/1996 | Cai et al. |
| 5,603,706 A | 2/1997 | Wyatt et al. |
| 5,607,393 A | 3/1997 | Ensminger et al. |
| 5,624,704 A | 4/1997 | Darouiche et al. |
| 5,653,696 A | 8/1997 | Shiber |
| 5,704,915 A | 1/1998 | Melsky et al. |
| 5,709,691 A | 1/1998 | Morejon |
| 5,718,899 A | 2/1998 | Gristina et al. |
| 5,789,115 A * | 8/1998 | Manev et al. ............... 424/423 |
| 5,803,078 A | 9/1998 | Brauner |
| 5,814,020 A | 9/1998 | Gross |
| 5,848,989 A | 12/1998 | Villani |
| 5,871,692 A | 2/1999 | Haire et al. |
| 5,882,329 A | 3/1999 | Patterson et al. |
| 5,902,283 A | 5/1999 | Darouiche et al. |
| 6,045,623 A | 4/2000 | Cannon |
| 6,050,976 A | 4/2000 | Thorne et al. |
| 6,056,717 A | 5/2000 | Finch et al. .................. 604/93 |
| 6,077,259 A | 6/2000 | Caizza et al. |
| 6,086,553 A * | 7/2000 | Akbik ....................... 604/175 |
| 6,086,555 A | 7/2000 | Eliasen et al. |
| 6,183,450 B1 | 2/2001 | Lois |
| 6,210,366 B1 | 4/2001 | Sanfilippo, II |
| 6,231,541 B1 * | 5/2001 | Kawamura ............... 604/93.01 |
| 6,258,058 B1 | 7/2001 | Sanfilippo, II |
| 6,352,521 B1 | 3/2002 | Prosl |
| 6,506,182 B2 | 1/2003 | Estabrook et al. |
| 6,520,978 B1 | 2/2003 | Blackledge et al. |
| 6,524,273 B2 * | 2/2003 | Kawamura ............... 604/93.01 |
| 6,530,900 B1 | 3/2003 | Daily et al. |
| 6,544,240 B1 | 4/2003 | Borodulin et al. |
| 6,562,023 B1 | 5/2003 | Marrs et al. |
| 2002/0069893 A1 | 6/2002 | Kawazoe |
| 2002/0156431 A1 | 10/2002 | Feith et al. |
| 2003/0060783 A1 | 3/2003 | Koole et al. |
| 2003/0065292 A1 | 4/2003 | Darouiche et al. |

FOREIGN PATENT DOCUMENTS

| | | |
|---|---|---|
| WO | WO 98/30249 A2 | 7/1998 |
| WO | WO 99/20338 A1 | 4/1999 |
| WO | WO 98/61093 A1 | 12/1999 |
| WO | WO 99/62576 A1 | 12/1999 |
| WO | WO 00/76577 A1 | 12/2000 |
| WO | WO 01/21251 A1 | 3/2001 |
| WO | WO 01/89607 A2 | 11/2001 |
| WO | WO 01/89607 A3 | 11/2001 |
| WO | WO 02/062414 A1 | 8/2002 |

* cited by examiner

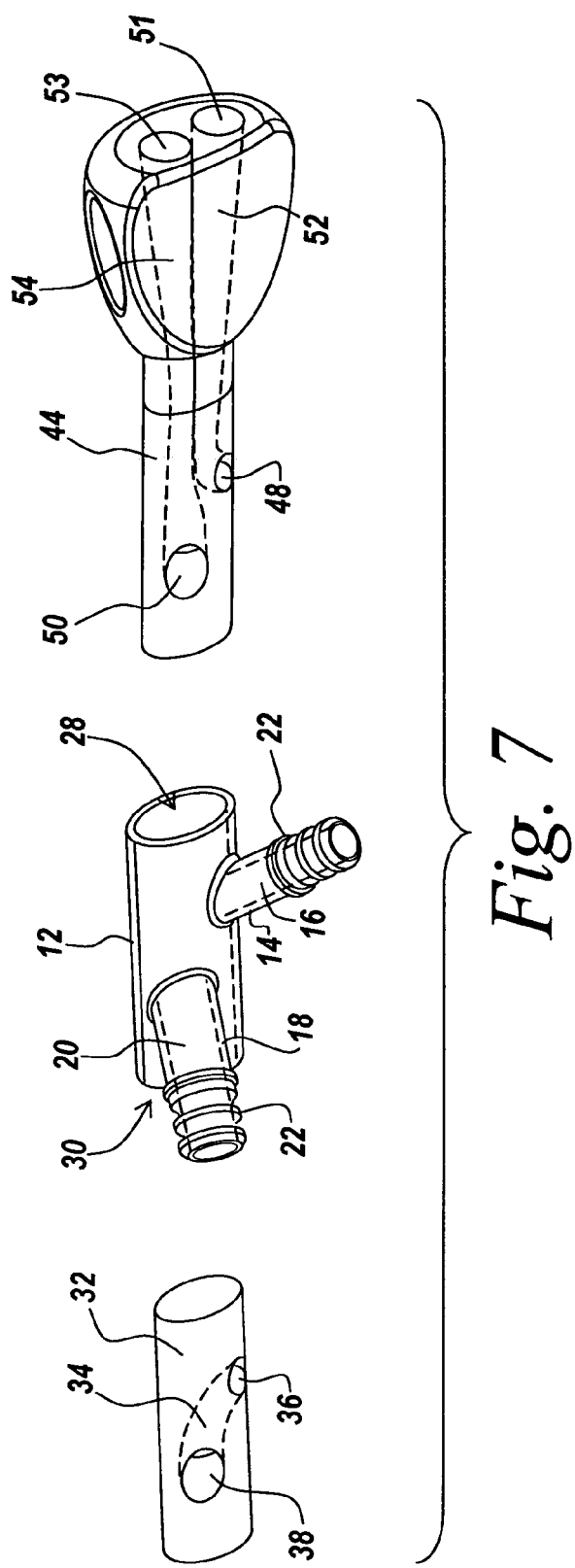

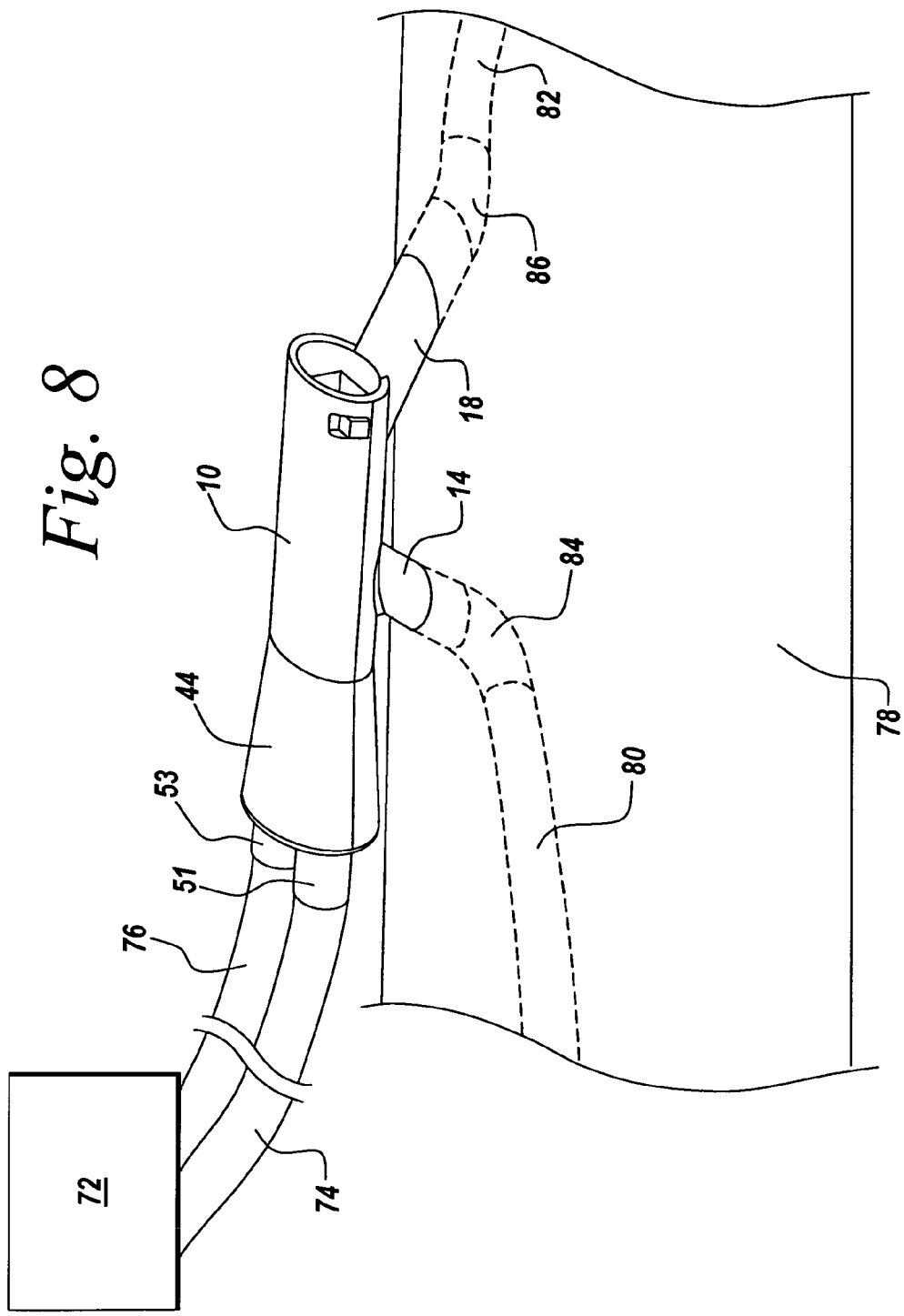

BODY FLUID CARTRIDGE EXCHANGE PLATFORM DEVICE

FIELD OF THE INVENTION

The present invention relates to a minimally invasive surgical implant that functions as an externally connectable body fluid cartridge exchange platform device.

BACKGROUND OF THE INVENTION

A number of patients today undergo recurring medical procedures requiring repeated skin penetrating access to the patient's internal hollow organs, including organs contained within the mediastinal, chest, abdominal and peritoneal cavities, and organs forming the patient's circulatory system, i.e., blood vessels. One such recurring medical procedure is hemodialysis. Currently, over one million patients worldwide suffer from End State Renal Disease (ESRD) conditions and require some form of daily or thrice weekly dialysis treatment via needle or catheter access. Peritoneal Dialysis is one form of dialysis treatment requiring needle or catheter access whereby fluids placed into the peritoneal cavity via a temporary or permanently placed access catheter provide osmotic transfer of blood containing toxins into solutions pumped into and removed from within the peritoneal organ cavity. A second form of dialysis treatment is a direct blood filtering process, whereby a needle or catheter is placed directly into a vein or artery, and through a series of connecting tubing, blood is removed and re-circulated back into the patient after filtration of the blood. These two hemodialysis procedures are the most common means for metabolic toxin removal from body fluids when a patient experiences total or bilateral renal failure.

Without needle or indwelling catheter organ access for dialysis, there is no physical connection means to conduct dialysis toxin removal, and the ESRD patients would die within days of total renal failure. Hence, the insertion method and form of dialysis connection access relates directly to the patient's ability to have body fluids contained within an internal organ communicate and be safely connected "externally outside the body" for the purposes of blood hemofiltration.

Because both types of dialysis treatment techniques discuss above require trained medical personnel for needle or catheter access and the administration of the actual external dialysis filtration process, there are significant healthcare hazards for both the patient and healthcare worker associated with such traditional needle access methods. Most ESRD patients must be transported to a public dialysis treatment center for treatment.

Some form of needle or indwelling catheter organ access is required as a physical connection means to conduct dialysis toxin removal. The insertion method employed and the form of dialysis access used affects the patient's ability to have body fluids contained within an internal organ communicate and be safely connected externally outside the body for the purpose of blood hemofiltration.

Most ESRD patients must travel to a public dialysis treatment center for treatment. Financial and logistical considerations are current sources of difficulty for an ESRD patient in obtaining necessary dialysis treatments. Consequently, any young or new ESRD patient must be placed into a treatment lottery, and may end up having to go for dialysis treatments at inconvenient hours (e.g., 2:00 AM to 6:00 AM). In addition, many patients are only being treated for a maximum of 3–4 hours per visit, and only 3 times per week.

Recent published studies have shown that "daily dialysis" treatment techniques bring many of these ESRD patient's blood toxicity levels down to normal, non-toxic levels. Thus, dialysis treatment approaching 3–4 hours per visit, three times per week, is inadequate for lowering patient toxicity levels to normal levels. Other studies have concluded that more frequent dialysis improves patient health and well-being, enabling patients to be more productive and lead a more independent life, while reducing reliance on medications and hours spent in the hospital. Reduction of time spent in hospitals helps the healthcare industry in that patient populations are growing at approximately 6%–7% annually, which could lead to a burden on our health care facilities.

Without a kidney transplant, the average life span of even the healthiest patient who has experienced total renal failure, is only about 5 years. It is now known from published clinical studies that when a patient can be treated "daily" with dialysis, even with shorter, less efficient periods of time on the dialysis machine, those individuals' blood toxicity levels return to near normal, and remain almost equivalent to their prior functional kidney performance levels. Often, the patients receiving daily dialysis no longer require the expense of erythropoietin-type medications to help stabilize their red blood cells during periods of blood toxicity. Erythropoietin is a significant cost to the patients, and it is required for dialysis patients who need to extend the survival half-life of their oxygen carrying red blood cells, especially under extreme blood toxicity conditions. Current indications are that more cost-effective daily dialysis will extend the survival rate of ESRD patients from a projected life expectancy of 5 years with 3–4 treatments per week, to about 20 years or more.

One of the common denominators relating to treatment cost with the ESRD patients is the need for a trained healthcare worker to clean, prepare, and install a needle, guide wire, or catheter into the body fluid organ access site for external connection of the dialysis tubing sets to the dialysis machine. Most dialysis patients require insertion of two large gauge dialysis needles directly through the skin and precisely into the body fluid organ, surgically installed graft, vein, or artery. Such a requirement means that for a patient to undergo dialysis treatment, they must travel to a center for a professionally trained healthcare worker to find the correct subcutaneous blood vessel location and then insert the access device needle or catheter precisely into the blood containing organ, without significantly damaging either the internal or external vessel wall surface. Without precision needle or catheter placement, a patient can bleed to death from a poorly placed needle or catheter. Other possible complications include total occlusion of the vessel, graft, or connection setup, requiring total access device removal and reinstallation elsewhere. Another common complication from needle or catheter access is the formation of a massive subcutaneous hematoma, which can become infected. The hematoma can require surgical intervention to drain, de-clot and repair, and sometimes results in death due to their already toxic blood conditions and compromised autoimmune protection system.

There are a number of complicating issues relating to the process of repeatedly sticking and cannulating a patient's circulatory organ system and removing/returning blood back to the patient. One significant complication is the need for maintenance of a sterile installation and connection technique for all components involved in establishing dialysis access through the patient's skin and into the hollow targeted organ, as well as connection to the dialysis tubing set, filter, and dialysis pump apparatus. Another complication is the inability of a particular artery or vein to be repeatedly cannulated or punctured at substantially the same convenient needle or catheter access site, due to vessel trauma, exit wound inflammation, dialysis graft complications, and/or enlarged needle hole formation resulting in massive needle hole bleeding/ hematoma formation. Repeated dialysis needle punctures create unwanted scar tissue formation and infection. Both conditions are directly related to repetitive needle and catheter cannulation through the skin. Such large gauge needle cannulation complications are uncomfortable for the patient and the healthcare worker, due to the associated pain of additional needle sticks. Infection complications of these needle access sites are difficult to treat, because of the constant migratory effects of nosocomial infections, which have been well documented to routinely originate from direct contact with topical skin sourced *Staphylococcocus* bacteria. These frequently occurring needle access complications often require surgical intervention to repair, reconstruct, or remove the affected vessel organ, in addition to requiring extended hospital admission and costly medication treatment with IV medications.

One approach to help solve some of these needle and indwelling catheter access complications, can be found in PCT Patent Application No. WO 99/20338 ("the '338 application"). The device of the '338 application is described as being an implantable metal port housing which is surgically installed within the body of a patient. The device includes a main body having two openings for connecting the implanted housing to blood vessels under the skin and or under the dermal layer of the patient. Implantation of the device requires a large surgical incision in the skin, separation or removal of a portion of the skin, insertion of the metal alloy housing or port can, attachment of the blood vessels to the implanted housing, and subsequent healing of the skin wound around the entire perimeter of the main housing body. The main housing body and blood vessel connecting portions of this device reside entirely below the dermal skin surface.

The device described in the '338 application has a main housing body and blood vessel connection means radiating from this housing that are positioned below the dermal skin layer, and may be subject to significant amounts of skin trauma, disruption, and inflammation surrounding the implanted device.

The main body of the device of the '338 application requires a flat or planar sealing surface to which a flat planar protective body lid or connecting member lid member seals. The lid then mounts to the housing via linear holding elements that press down onto and deflect holding means on the protective body to establish a sealable surface with the main housing sealing surface. The lid holding means are described as being sideways-directed linear flanges to cooperate with holding elements on the main body. The '338 application further states that the holding elements must be deflected to function. The holding elements, as described, push down and deflect the linear flanges to keep tension on the flat and planar protective body lid to maintain a sealable surface. This holding element and the holding means are the only described mechanisms for maintaining a sealable surface to the main housing's flat and planar sealing surface. To change a lid, an attachable linear slide holder, tool, or cassette, fits over an exposed portion of the indwelling main body outer surface and protruding holding elements to allow the simultaneous change-out of the protective body lid as it is guided by the straight planar holding elements located on top of the exposed outer surface of the main body housing. The protective body lid is displaced in a one-way linear push fashion by another connecting member lid with identical holding means using mechanical lever assistance in the holder, tool, or cassette device. The linear slide tool with mechanical lever assistance for protective lid replacement or exchange is then removed from the main body with the used protective lid held onto the skin contacting surface of the linear slide tool for their combined disposal.

As a large indwelling implant, the access port design of the '338 device has no means for remote incision placement for the blood vessel attachment legs or connection means. The device housing and blood vessel connection legs must sit directly on top of, or within, the surgically exposed sub-dermal tissue location. Installation connection of an outwardly directed tube connection means of the '338 device requires blunt dissection into the sub-dermal tissue directly under, or to, the immediate side area of the installed main housing body, clearly below the surface of the skin. The main housing body of the '338 device after surgical installation may also be sensitive to touch and/or be painful to topical depression or compression by the patient, due to direct main housing body contact with subdermal tissue, and the potential for chronic inflammation in, under, and around the neighboring tissue following implantation. Such compromising issues may be further exasperated by poor wound tissue healing at both the housing/dermal skin contact zone, and/or the tissue contact zone directly under the implanted metal port can, as there is no disclosure of providing a microporous healable cuff material for tissue incorporation. With such large non-porous metal surfaces, there is little or no biological attachment of healing tissue to help stabilize movement of the main body of the '338 device. Without healthy remodeled collagen producing tissue growth to help stabilize the housing of the '338 device, tissue will remain swollen and inflamed. Due to the potential size requirements to fabricate a flat and planar sealable surface mechanism, the risk of dermal compression about the perimeter of the indwelling metal device could lead to necrosis of the surrounding tissue, which can only be treated by surgical removal, followed by skin graft reimplantation to replace the lost dermal skin over the effected area.

In the presence of any implanted device or sub-dermal wound infection, aggressive medical treatment for adjacent contacting tissues about the indwelling structure requires lengthy treatment periods with powerful intravenous or intramuscular injectable antibiotics, and/or complete surgical removal of the implant. Failure to diagnose and treat device-related infections could easily lead to tissue necrosis in, under, and around the implanted main body housing. Even if there were no visible or apparent physical signs of device infection, substantial sub-dermal inflammation in and around, and directly under the main housing of the '338 device would over time likely result in subsequent infection, principally due to the massive amount of tissue healing and collagen tissue remodeling required to stabilize the non-cell porous implantable structure. Historically, published studies on similar implantable metal port structures indicate that recurring infection and chronic inflammation can also lead to other life threatening conditions and systemic blood problems, such as endocarditis, bacteremia/septicemia, and/ or hypercoagulation and thrombosis.

Another known device is described in U.S. Pat. No. 5,474,526. A substantial portion of the main housing of this device disclosed in the '526 patent is again implanted completely within the body of the patient with the exception of an outer rim portion of the main implanted body housing extending outward through the skin. The '526 device has many of the same device requirements as the '338 device.

An outward coupling means achieves a connection to the housing by rotation of a stop-cock like connecting member relative to the housing after axial insertion to one exposed open end of the indwelling the housing. A coupling means makes the connection between the artery and vein of the patient and the external apparatus, such as a dialysis machine. The implanted device is substantially indwelling to the skin and connected to the blood vessels by port members which radiate from the main body housing below the surface of the skin, which essentially results in a totally subcutaneously implanted device. In similar fashion to the '338 device, the '526 device is likely to experience significant displacement of skin and dermal tissue. The same concerns for infection are likely to occur with this same non-porous metal housing construction, with bacterial colonization spreading from one surface plane of the '526 main body housing within the large installation incision to another indwelling surface plane, followed by inflammation of the localized tissue around and under the implantable metal housing. Neither the '338 patent, nor the '526 patent, teach or suggest provisions for limiting the amount of implantable material surface area for reduced surgical installation tissue dissection, or tissue disruption. Further, neither the '338 patent device, nor the '526 patent device descriptions provide design elements or surgical installation considerations for encouraging remote wound incisions to help improved healing after implantation or help control or minimize main body housing infection with such port devices. Additionally, neither patent describes material specifications for maximizing tissue attachment to the implanted main body housing for well-anchored, collagen remodeling dermal tissue.

SUMMARY OF THE INVENTION

There is a need for an implantable organ access device requiring a minimal amount of disruption to the patient's skin for implantation, and thus significantly reducing the amount of device surface area penetrating the skin and creating wounds that require healing. There is a further need to reduce the material surface area and size of a surgically installed portion of a body fluid cartridge exchange platform and to offer a mechanically simplified, needle less, and easy to use external body fluid organ connection device. Such a device requires minimal surgical disruption of the patient's outer dermal and sub-dermal tissue, and thus significantly reduces the amount of tissue trauma and wound size for faster, more efficient wound healing. There is a further need for an implantable tubular cartridge exchange platform mechanism for external connection and fluid communication means, with a positive locking and leak-proof connection means to such known therapeutic body fluid handling devices as a dialysis blood filtration machine, cardiopulmonary blood oxygenator system, therapeutic cell washing and blood transfusion processing equipment, and/or attachment to a long term drug delivery apparatus for chronic administration of chemotherapeutic agents.

Applicable devices further significantly reduce the amount of material mass and surface area to be surgically installed below the surface of a patient's skin to help reduce the risk of bacterial colonization from occurring in, under, or around, the sub-dermal implanted portions of the surgically installed device. An elegantly simple mechanical cartridge exchange platform serves to improve the safety of repetitive patient dialysis tubing connection, without the documented patient risks and hazards associated with repetitive "needle sticking" and/or patient health complications associated with invasive and repetitive vascular graft or blood vessel cannulation. Further, such a body fluid cartridge exchange platform also serves to improve patient safety, and simplify the mechanical connection process to such internal organs with less wound complications, which are serious and sometimes life threatening complications associated with other known implantable metal port access devices.

The present invention provides solutions to address these needs, in addition to simplifying access to the patient's body fluid and external medical treatment connection technique, with a potentially more cost efficient body fluid cartridge exchange platform device, that can further expand the clinical use and application of "daily dialysis" patient care in addition to other needs not specifically mentioned.

In accordance with one example embodiment of the present invention, an implantable body fluid cartridge exchange platform device is provided. The implantable body fluid cartridge exchange platform device has a hollow cartridge platform housing with a first end having an opening. The hollow cartridge platform housing additionally has a second end with a second opening. The first opening and the second opening facilitate bi-directional insertion of a tubular cartridge insert that sealably engages inside the hollow cartridge platform housing. The first opening and the second opening additionally facilitate bi-directional removal of the interchangeable tubular cartridge insert.

In accordance with one embodiment of the present invention, the hollow cartridge platform housing includes a first hollow leg member having an internal diameter suitable for extending out from the hollow cartridge platform housing and through the skin of a patient. The first hollow leg member can have an external cross-section area of less than 10 mm, causing the member to be a small diameter skin penetrating element of the hollow cartridge platform housing. The first hollow leg member facilitates fluid communication between an internal body fluid organ and the hollow cartridge platform housing, which resides horizontally above the surface of the patient's skin. The small diameter first hollow leg member additionally supports the under surface of the hollow cartridge platform housing up and away from the surface of the patient's skin.

In accordance with still another embodiment of the present invention, a tubular cartridge insert provides an internal cartridge flow path lumen, channel, or passageway, through a portion of the tubular cartridge insert. The tubular cartridge insert's internal cartridge flow path lumen has an internal flow path diameter dimension varying from a diameter dimension relatively greater than the internal diameter dimension of the first hollow leg member to substantially a same diameter dimension as the internal diameter of the first hollow leg member. In addition to the first hollow leg member, a second hollow leg member is provided extending out from the hollow cartridge platform housing through the skin of the patient. The second hollow leg member can have an external diameter cross-sectional area of less than 10 mm, causing the second hollow leg member to be considered a small diameter skin penetrating element of the hollow cartridge platform housing. The second hollow leg member completes a fluid communication path extending between the first hollow leg member and the second hollow leg member through the internal cartridge flow path lumen of the tubular cartridge insert. The second hollow leg member additionally supports the under side surface of the hollow cartridge platform housing up and off the surface of the patient's skin.

In accordance with further embodiments of the present invention, the first and second hollow leg members include multiple internal lumens that communicate with one or more tubular cartridge insert internal cartridge flow path lumens. The multiple internal cartridge flow path lumens can communicate with one or more discretely different organ locations or sections, and/or communicate with two or more distinctly different body fluid organs.

In accordance with still another embodiment of the present invention, the tubular cartridge insert includes a locking mechanism for positively locking and/or containing the tubular cartridge insert into a fixed location within the hollow cartridge platform housing. Several different mechanical methods can be used to temporarily lock, contain, or hold the tubular cartridge insert into a desired position within the hollow cartridge platform housing. One example of a temporary locking mechanism can take the form of, e.g., a flexible tab element that extends from and beyond a sealable surface portion of the tubular cartridge insert that is located inside a portion of the hollow cartridge platform housing. A portion of the locking tab element can be made to fit into a receiver located in a portion of the hollow cartridge platform housing wall surface once the tubular cartridge insert reaches a desired fixed position within the hollow cartridge platform housing. The hollow cartridge platform housing can include a receiver for accommodating, containing, and positively locking the flexible tab in a temporary and fixed position to hinder movement of the tubular cartridge insert once it has obtained its intended position within the hollow cartridge platform housing.

In accordance with another embodiment of the present invention, one or more tubular cartridge inserts sealably engage with a portion of an inside surface of the hollow cartridge platform housing with internal fluid path port opening alignment with each of the hollow leg members, to provide body fluid communication with each of the first and second hollow leg members.

In accordance with still another embodiment of the present invention, the tubular cartridge insert further includes an external communicating passageway or lumen, which extends from a first port opening along the internal cartridge flow path lumen and out through a second port opening on one end of a non-sealable tubular cartridge insert surface.

In accordance with yet another embodiment of the present invention, a body fluid cartridge exchange platform device for providing external needleless connection and fluid communication to internal body fluid organs is provided. The cartridge exchange platform device includes a tubular housing having a first opening at a first end and a second opening at a second end. A tubular exchange cartridge insert sealably engages a portion of the hollow cartridge platform housing to maintain a leak-proof seal for all body fluid communicating internal flow paths, channels, and/or passageways within the hollow cartridge platform housing. The tubular exchange cartridge insert is installed right side up to attain body fluid communication after installation inside the hollow cartridge platform housing and therefore is made to prevent incorrect installation, by the installation assistance of a second, pre-loaded cartridge insert exchange tool or device. The cartridge insert exchange tool is also made for bi-directional movement into and out of the tubular cartridge platform housing, including installation and/or removal through either of end of the first and second openings of the cartridge platform housing.

In accordance with another embodiment of the present invention, the hollow cartridge platform housing further includes a first hollow leg member having at least a first distal port opening in communication with a first proximal port opening, and a second hollow leg member having at least a second distal port opening in communication with a second proximal port opening. The first hollow leg member and the second hollow leg member can each extend outward from an outer wall surface of the hollow cartridge platform housing. The first hollow leg member position location can be staggered and divergent away from the second hollow leg member along the same wall surface of the cartridge platform housing.

In accordance with still another embodiment of the present invention, the hollow cartridge platform housing further includes a first leg member having at least a first open passageway, an internal flow path, or channel, in communication with the first port opening and a second leg member having at least a second open passageway in communication with the second port opening. The first leg member and the second leg member can each extend outward from the outer wall surface of the hollow cartridge platform housing. The first leg member position can be staggered and divergent away from the second leg member along the same wall surface of the hollow cartridge platform housing to provide unrestricted body fluid flow in and out of the hollow cartridge platform housing insert assembly.

In accordance with further embodiments of the present invention, the hollow cartridge platform housing further includes an internal flow path, channel or passageway disposed into the cartridge tubular cartridge insert or along a portion of the sealing surface of the cartridge insert, for the purpose of providing body fluid communication from a first hollow leg member proximal port opening and to a second hollow leg member proximal port opening, when the first and second sealing surface port openings and internal flow path of the cartridge insert come into alignment at an intended fixed position to complete a fluid circuit within the hollow cartridge platform housing. The internal flow path, channel, or passageway in the tubular cartridge insert completes a circuit between the first and second port openings disposed within a portion of the sealing surface of the tubular cartridge insert, and the first and second hollow leg member proximal port openings located in the inner wall surface of the hollow cartridge platform housing. The tubular cartridge insert with the body fluid communicating internal flow path, channel, or passageway disposed into the sealing surface or made part of the sealing surface, can further include at least one external passageway or lumen that communicates with an external port opening on the surface of the internal flow path and communicates with an external port opening located on one non-sealable external surface of the tubular cartridge insert. The external passageway or lumen is suitable for introducing, removing or re-circulating body fluid or other bioactive fluid or injectable substance. There can additionally be one or more external passageways or lumens extending from and or communicating with the cartridge insert internal flow path, channel, or passageway, to one or more external port openings located on an external non-sealable surface of the cartridge insert. Multiple external fluid communicating passageways, lumens can also communicate with two or more external non-sealable surfaces of the cartridge insert.

In accordance with further embodiments of the present invention, the body fluid cartridge exchange platform device further includes an internal flow path, channel, or passageway disposed along the sealable surface of the tubular exchange cartridge insert for the purpose of providing unrestricted body fluid flow from the first hollow leg member communicating with an organ communicating to the second hollow leg member communicating with a second organ. The body fluid channel completes a flow path between a first passageway opening and a second passageway opening through the first and second port openings within the sealable surface of the hollow cartridge platform housing. The tubular exchange cartridge insert with a body fluid communicating channel along its sealable surface can further include at least one external passage or lumen that communicates from a port opening along the surface of the body fluid channel and out to a port opening located on at least one non-sealable external surface of the tubular exchange cartridge insert. The external passage lumen is suitable for introducing or removing body fluid or another bioactive substance. There can additionally be one or more external passageways or lumens in communication with the body fluid channel and to one or more port openings located on the same non-sealable external surface of the tubular exchange cartridge insert. Such external passageways or lumens can also exit out to two or more non-sealable surfaces of the tubular exchange cartridge insert. The tubular exchange cartridge insert can further include a first open body fluid channel port and a second open body fluid channel port at opposite ends of the channel. The distance between the first channel port and a first end of the tubular exchange cartridge insert is greater, in accordance with the one embodiment of the present invention, than a diameter of the first channel port. In addition, the distance between the second channel port and the second end of the tubular exchange cartridge insert is greater than a diameter of the second channel port.

The tubular cartridge insert can further include a first sealing surface port opening and a second sealing surface port opening at opposite ends of a body fluid communicating internal flow path, channel, or passageway. The distance between the first sealing surface port opening and a first external non-sealing surface end of the tubular cartridge insert in accordance with one embodiment of the present invention, is greater than the diameter of the first sealing surface port opening. In addition, the distance between the second sealing surface port opening and the second non-sealing surface end of the tubular cartridge insert is greater than a diameter of the second sealing surface port opening to facilitate leak-proof movement, displacement or exchange of the tubular cartridge insert by another cartridge insert.

A portion of the first and second hollow leg members penetrate and reside within the skin of a patient when the body fluid cartridge exchange platform device is surgically implanted in accordance with one embodiment of the present invention. The first and second hollow leg members further support the raised hollow cartridge platform housing distally, in a raised condition up and off the surface of the skin. In accordance with one embodiment of the present invention, the first passageway and distal port opening of the first hollow leg member and the second passageway and distal port opening of the second hollow leg member are both in fluid communication with the same body fluid organ, or each independent hollow leg member can be in fluid communication with two distinctly separate body fluid organs and/or two remotely located similar body fluid organs of the patient.

In accordance with still further embodiments of the present invention, the appropriately sized and matched body fluid tubular cartridge insert and hollow cartridge platform housing have a generally oval cross-section and uniform sealable contact surface relative to each other to provide precision cartridge component surface alignment to the sealable contacting surface of the hollow cartridge platform housing. It will be further understood that such a tubular oval shape also provides radial alignment of all sealing wall surface and sealing surface port openings inside the hollow cartridge platform housing. The tubular form and oval shape maintains sealing surface engagement between the tubular cartridge insert and the hollow cartridge platform housing simultaneous to preventing cartridge insert misalignment by rotation, for maximum body fluid communication alignment and patient safety.

In accordance with another example embodiment of the present invention, a mechanically simplified, externally connectable body fluid cartridge exchange platform device is provided. The body fluid cartridge exchange platform device has a hollow tubular receiving lumen with a first end having an opening. The body fluid cartridge exchange platform device additionally has a second end having an opening. Each open end of the tubular receiving lumen facilitates insertion of a matching tubular cartridge insert that fits into and sealably engages within the tubular receiving lumen. Both the first and second platform housing openings additionally facilitate bi-directional removal of an installed tubular cartridge insert by direct contact of at least one non-sealable surface of the tubular cartridge insert, and forceful displacement by a another interchangeable or replacement tubular cartridge insert's non-sealable surface.

BRIEF DESCRIPTION OF THE DRAWINGS

The aforementioned features, patient benefits, clinical advantages, in addition to many other physical and mechanical features and aspects of the present invention, will become better understood with regard to the following description and accompanying drawings, wherein:

FIG. 7 is a perspective bottom view illustration of the body fluid cartridge exchange platform device displaying first and second hollow leg members with first and second distal port openings, and the two different cartridge inserts of FIG. 6 displaying the respective annular sealing surface port openings on the sealable surface of each cartridge insert according to one embodiment of the present invention;

FIG. 8 is a diagrammatic illustration of portions of an implanted cartridge platform device that reside above or distal to the patient's dermal skin surface, and portions of the cartridge platform housing which penetrate and reside below the patient's skin surface, and a cartridge insert that is connected external to and in fluid communication with an example life supporting machine, such as a dialysis blood filtration apparatus, according to one embodiment of the present invention;

DETAILED DESCRIPTION

Figure 1:
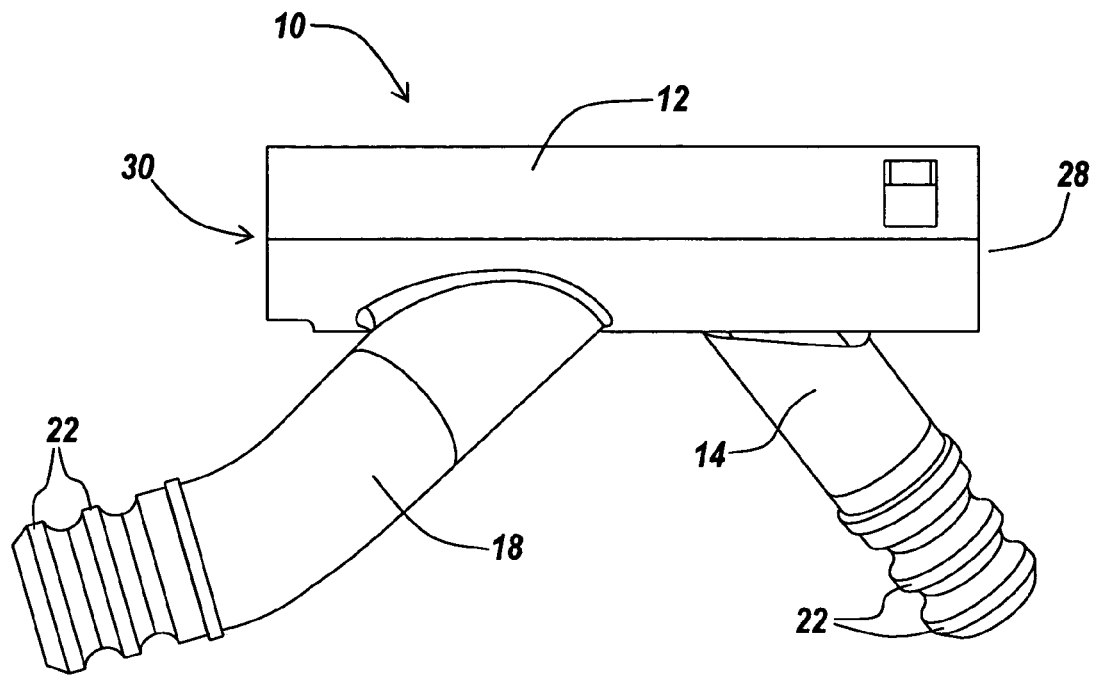
FIG. 1 is a diagrammatic illustration of a cartridge exchange platform device according to one aspect of the present invention.

An illustrative embodiment of the present invention relates to a minimally invasive and percutaneous implantable body fluid cartridge exchange platform device to provide leak-proof body fluid communication between one or more internal organs and simplified external medical treatment connection to one or more internal body fluid organs. One example of a body fluid organ, for purposes of clarity in describing the invention, is characterized as a blood vessel herein. Nevertheless, those skilled in the art will appreciate the present invention may be used with other internal body fluid organs and the invention is not limited to applications for use with those organs in fluid communication with blood vessels.

The device referred to as the body fluid cartridge exchange platform device includes two or more hollow leg members extending out from a hollow cartridge platform housing and penetrating through two or more separate and remotely located percutaneous wounds or incisions of the patient. Hollow leg members are in fluid communication with one or more blood vessels of the patient. For example, a first hollow leg member can be in fluid communication with an artery and a second hollow leg member can be in fluid communication with a vein. The use of the two small diameter leg members to extend downward through two separate small wound incisions of the skin surface reduces the amount of surgical disruption and displacement of skin tissue following device implantation. The use of two small diameter percutaneous leg members reduces the amount of skin tissue dissection and inflammation about the device during wound and skin surface healing when compared to larger skin penetrating port access devices, which can be more difficult for skin tissue to stabilize with collagen remodeling tissue following implantation. In addition, utilizing two or more small diameter percutaneous leg members rather than one large skin protruding device, provides more natural movement of the patient's skin around portions of the leg members and the raised hollow cartridge platform housing following wound healing. The use of two or more, small diameter hollow leg members instead of one large skin protruding main body housing also significantly reduces the amount of foreign body material and mass, as well as device surface area that can reside in direct physical contact with surgical wound tissue, thus significantly reducing the size and scope of tissue dissection required for implantation. The reduction in the wound size and scope of wound dissection significantly improves the rate and completeness of wound healing, significantly improves the overall strength and flexibility of the healed skin tissue due to less scarring about the small diameter leg members of the cartridge exchange platform device, and reduces wound complications such as inflammation and infection due to less material mass. In addition, separation or distancing of each small diameter leg members' wound incision, one independent incision for each leg member, reduces the likelihood of infection at a first leg member location from spreading or migrating to the second leg member location, thus improving the patient's treatment options for better wound healing outcomes.

The hollow leg members support the cartridge platform housing and first and second housing openings up, off, and away from direct contact with the topical surface of the patient's skin. This raised cartridge platform housing arrangement also creates a boundary of healthy skin between the two leg members and underneath the cartridge platform housing to help protect the wound incisions and make the topical area under the cartridge platform housing accessible for daily hygiene care. By allowing all externally cleanable surfaces above, under, and around the platform housing, including those portions of the leg members that do not come into direct contact with the patient's skin during normal physical activity, daily hygiene and skin care can easily be accomplished by washing and swabbing in and around all externally cleanable surfaces of the cartridge platform device. Raising all cartridge insert contact surfaces, cartridge platform housing openings, cleanable surfaces, and internal tubular sealing surfaces distal to the patient's skin, further prevent contamination of the cartridge insert during cartridge exchange. Such a cartridge platform device also significantly reduces the risk and likelihood of any body fluid communicating internal flow path, channel, or passageway from becoming contaminated by direct or physical contact with the patient's skin during use. The generally horizontal orientation of the cartridge platform housing and the first and second tubular platform housing openings being raised up and off the surface of the skin in a generally horizontal orientation to the skin surface, together with the use of the sterile cartridge platform exchange tool, provides a contaminant free, cartridge insert exchange or change-out technique. The raised cartridge platform arrangement of the implanted device keeps all internal body fluid communicating flow paths and all interior sealable wall surfaces of the cartridge platform device free from direct contact with the sometimes infected or contaminated skin surface. The body fluid cartridge exchange platform device significantly reduces the likelihood of circulating body fluid from becoming contaminated by direct exposure to topical skin bacteria during cartridge exchange, and further limits the patient's exposure to infection caused from internal body fluid contact with topical skin sourced bacteria, e.g. *Staphylococcus* bacteria including *Staph. Aureus* and *Staph. Epidermis*.

In accordance with one embodiment of the present invention, the body fluid cartridge exchange platform device includes a tubular housing with an interior sealing surface having two openings, one at each end. The existence of the two horizontally oriented tubular openings enables a patient, family member, or healthcare worker, to bi-directionally insert, exchange and or remove the tubular cartridge inserts.

The tubular and generally oval shaped cartridge inserts can be constructed of one or more assembled elements or parts to form one leak-proof tubular cartridge unit, or formed as a multi-cartridge, leak-proof assembly unit. The cartridge insert can easily be inserted, displaced, and removed out through either open end of the cartridge platform housing by forward directed contact and displacement from insertion of a second cartridge insert and use of a sterile cartridge exchange tool.

FIGS. 1 through 10B, wherein like parts are designated by like reference numerals throughout, illustrate an example embodiment of a body fluid cartridge exchange platform device according to the present invention. Although the present invention will be described with reference to the example embodiment illustrated in the figures, it should be understood that many alternative forms can embody the present invention. One of ordinary skill in the art will additionally appreciate different ways to alter the mechanical sealing surfaces, geometry, and biological interfacing parameters of the embodiments disclosed, such as the size, shape, biocompatibility, mechanical locking and release mechanisms, internal flow path orientation, external attachment and connection means, sealable wall surface engagement, mechanical construction and assembly, electromechanical body fluid sensor means, or type of materials and or construction methods used to manufacture and package such a device, in a manner still in keeping with the spirit and scope of the present invention.

FIG. 1 illustrates a diagrammatic side view of a body fluid cartridge exchange platform housing, (platform housing 12). A body fluid cartridge exchange platform device 10 tubular and generally oval shaped platform housing 12. The platform housing 12 is substantially hollow, and as shown in later illustrations, has a generally oval cross-section, although other cross-section profiles are possible. There is a first small diameter hollow leg member 14 extending out from the platform housing 12 in a first direction, and a second small diameter hollow leg member 18 extending out from the platform housing 12 in an angled and divergent direction relative to the first leg member 14. The first leg member 14 and the second leg member18 angle away from each other. The angles of each leg member 14 and 18 ease the surgical installation or implantation of a portion of the leg members 14 and 18, which penetrate through and reside within two small and separate wound incisions. The divergent angles of the hollow leg members 14 and 18 and their corresponding internal flow path, channel, and/or fluid passageway 16 and 20 reduce the occurrence of flow restrictive corners in the transition flow path, channel, or passageway located inside an aligned cartridge insert within the cartridge platform housing 12.

Taking the example of body fluid flow in a patient's blood vessels, each vessel runs generally parallel along the straight line direction of, e.g., the patients arm, leg, torso, or internal body cavity. It is desirable when body fluid is to be removed and or re-circulated back into the patient's arm for the body fluid within the cartridge platform device to follow a generally straight line flow path that angles up and away from the surface of the arm, then returns back into the patient at the same generally straight line flow path and divergent angle. Thus, the angle of the platform leg members 14 and 18 directs the flow of blood away in a generally straight line flow path from the body fluid organs or blood vessels, and returns the blood to back to the blood vessels in the same generally straight line direction, without using sharp angles that could cause undue fluid turbulence and fluid damage. Sharp, hard edge angles can adversely affect the natural flow dynamics of the blood, and damage fragile blood cell components, in addition to inducing chemical activation of certain blood containing components such as platelets, and circulating fibrinogen.

Each leg member 14 and 18 can take the form of a separate component fixedly coupled to the platform housing 12 by conventional means, such as adhesive, welding, thread connections, or equivalent leak-proof coupling means. Alternatively, the platform housing 12 can be formed with the leg members 14 and 18 included, forming the platform housing 12 and the leg members 14 and 18 as a single monolithic housing. In addition there can be a number of leg members other than two, such as a single skin penetrating leg member that bifurcates into two body fluid flow paths below the surface of the skin, or a plurality of leg members greater than two that percutaneously enter through the skin independently. The ultimate clinical purpose set for the particular cartridge exchange platform device 10 will dictate the actual number of housing leg members required to carry out the intended clinical purpose and or body fluid communication requirement. If, for example, four blood vessels are to be connected to the cartridge exchange platform device 10, the device 10 may require four leg members.

The first leg member 14 and the second leg member 18 each include one or more annular ridges, depressions, diverging grooves, or faceted wall surfaces 22 disposed on a portion of each leg member 14 and 18 external wall surface. The external annular ridges 22 facilitate one method to maximize the mechanical connection strength of the first and second leg members to either natural tissue or to medical grade tubular materials such as those synthetic and biologic materials commonly used in forming leak-proof body fluid connections with blood vessels or other body fluid communicating organs within a patient. For example, the leg member ridges 22 enable a synthetic or biological vascular graft material, and/or a piece of medical grade tubing to grasp securely onto the annular ridges of each leg member 14 and 18, to hinder undesirable slippage, removal, or disconnection from the platform housing leg members 14 and 18. The biological vascular graft material can take the form of a microporous healable cuff (e.g., first and second organ communicating means 84 and 86 shown in FIG. 8). The microporous nature of such a cuff enables cell penetration to further stabilize a coalescing of the cuff with body tissue to hold the body fluid cartridge exchange platform device 10 in place.

The platform housing 12 additionally includes a first opening 28 at a first end of the platform housing 12 and a second opening 30 at a second end of the platform housing 12. The first opening 28 and the second opening 30 provide bi-directional access into the hollow tubular interior and sealably engaging wall surfaces of the platform housing 12. The platform housing 12 interior wall surface extends in a generally straight line along a length between the first opening 28 and the second opening 30 as illustrated. However, the platform housing 12 can also follow a slightly arcuate path between the first opening 28 and the second opening 30 if desired, so long as any cartridge insert that is made to match and fit within the hollow tubular wall surface portion of the platform housing 12 maintains a leak-proof seal with a portion of the platform housing's arcuate shape, and/or flexes uniformly to maintain a leak-proof seal with a portion of the same generally arcuate tubular platform housing shape.

The platform housing 12 and the first and second leg members 14 and 18 can be made from a single material, or from a blend of two or more similar materials, or be constructed from two or more distinctly different materials, including the use of several layers or coatings of similar or dissimilar formable materials, such as biocompatible Class IV, or equivalent medical grade, and/or body fluid compatible plastics, e.g. PEEK, PET, Acrylic Co-Polymers, PTFE, PVC, Synthetic Elastomers and or Polycarbonate.

The dimensions of the example embodiment are determined primarily by the value of the internal diameter of the internal leg members 14 and 18. More specifically, the internal diameter of the internal leg members 14 and 18 requires a minimum internal diameter passage for the path connecting the two internal leg members 14 and 18 as later described herein. The minimum size for the path subsequently dictates the overall size of the body fluid cartridge exchange platform device 10. For example, if the internal diameter of the internal leg members 14 and 18 was between 2 mm and 4 mm, the path would be smaller than if the internal diameter was between 3 mm and 5 mm. Thus a relatively smaller body fluid cartridge exchange platform device 10 would be required. These are example measurements that are by no means intended to limit the dimensions of the present invention. One of ordinary skill in the art will appreciate that the particular purpose for which the invention is used will dictate the size of the internal leg members 14 and 18, and thus the overall size of the body fluid cartridge exchange platform device 10.

These internal platform housing 12 dimensions and internal leg member 14 and 18 dimension ratios illustrate a few examples of an appropriate sized and small diameter leg member cartridge exchange platform device 10. However, the dimensional platform housing 12 sizes and leg member 14 and 18 dimensional size ratios can vary, as understood by one of ordinary skill in the art, as different implant locations, specific anatomical conditions, clinical purpose and flow requirements, cartridge insertion requirements, and or sealing surface requirements can determine the actual dimensional size requirements for each clinical purpose and the method of use for the body fluid cartridge exchange platform device 10.

Figure 2:
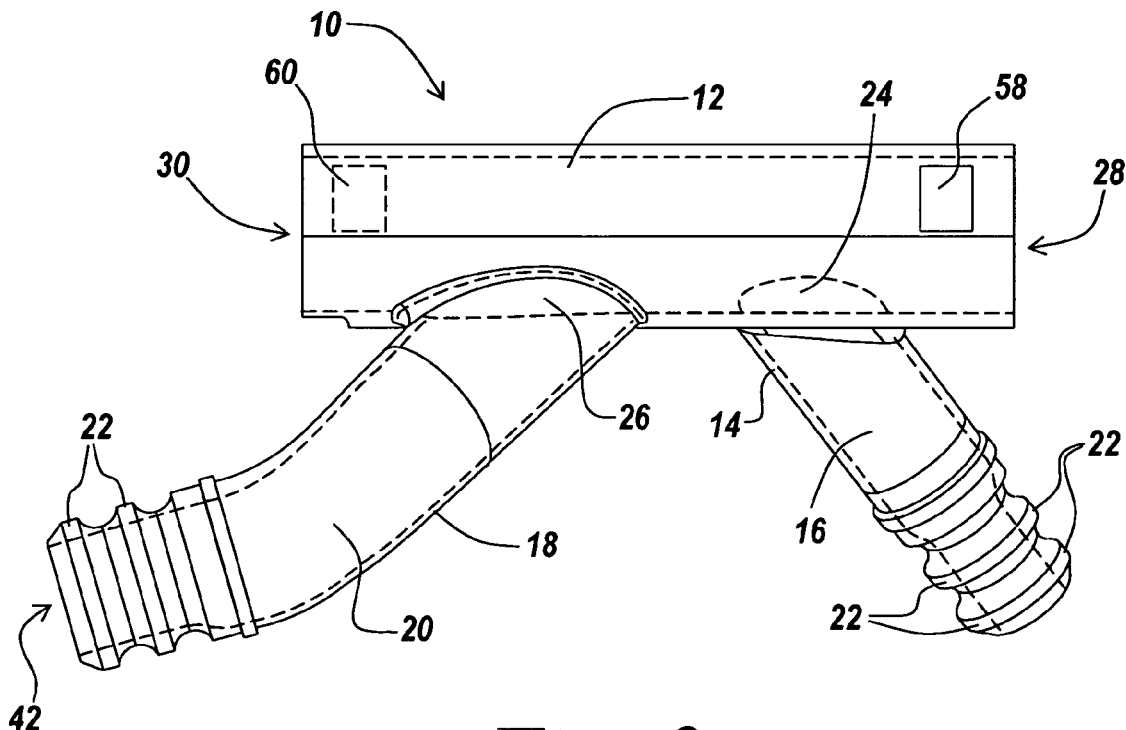
FIG. 2 is a diagrammatic illustration of the cartridge exchange platform device according to a further aspect of the present invention.

FIG. 2 illustrates an example of the platform housing 12 with two independent tubular leg members 14 and 18, and the internal fluid passageways 16 and 20 located inside the two hollow leg members 14 and 18, along with first and second leg member distal port openings 40 and 42, and first and second leg member proximal port openings 24 and 26 of FIG. 1 in phantom form. The platform housing 12 includes the first leg member 14 and the second leg member 18 attached thereto. The platform housing 12 further includes the first leg member proximal port opening 24 in the interior sealing wall surface of the platform housing 12. The first leg member proximal port opening 24 provides body fluid communication to an interior wall surface portion of the hollow platform housing 12. The platform housing 12 also includes the second leg member proximal port opening 26 in the interior wall surface of the platform housing 12. The second leg member proximal port opening 26 also provides fluid communication to an interior wall surface portion of the platform housing 12. The second proximal port opening 26 can be located diagonally offset from the first proximal port opening 24 on the same interior wall surface of the platform housing 12, or placed at a different radial location from the first proximal port opening 24 of the same interior wall surface of the platform housing 12, and/or can be located anywhere along the interior sealing wall surface of the platform housing 12 so as to provide cartridge insert sealing surface engagement inside the tubular platform housing during cartridge insert movement, exchange and/or displacement by forward directed contact and movement from a second cartridge insert, which will be disclosed further herein (see FIGS. 5A, 5B, and 5C).

The first leg member 14 includes the first internal passageway 16, and the second leg member 18 includes the second internal passageway 20. The first internal passageway 16 extends from the first leg member proximal port opening 24 to the first leg member distal port opening 40. The second internal passageway 20 extends from the second leg member proximal port opening 26 to the second leg member distal port opening 42. The first and second leg member distal port openings 40 and 42 provide fluid communication into and out from the cartridge exchange platform device 10, from one or more body fluid organs of the patient, depending on the particular clinical purpose and requirement for the body fluid cartridge exchange platform device 10.

The platform housing 12 additionally includes a first positive locking tab receiver 58 disposed in one interior and tubular sealing wall surface. For selected clinical applications and uses, more than one positive locking tab receiver 58 may be required. Therefore a second positive locking tab receiver 60 can be disposed into the interior sealing wall surface of the platform housing 12, at a second interior sealing surface location. In accordance with one embodiment of the present invention, two locking tab receivers 58 and 60 can be located independently and at opposite ends of the platform housing 12 to each other, and/or located at opposite sides of the platform housing 12 to each other, or further can be located side by side to each other in any orientation within the same radial orientation of tubular sealing wall surface of the platform housing 12. The first receiver 58 and the second receiver 60, as illustrated in the embodiment shown, are in the form of rectilinear apertures through the wall of the platform housing 12. The first and second receivers 58 and 60 accommodate a portion of the cartridge insert locking tab 62, which extends out from and beyond the radial tubular sealing surface of a cartridge insert 32 or 44, and the tubular cartridge insert reaches its intended fixed destination location within the platform housing 12. Further descriptions of the cartridge insert locking tab mechanism 62, will be discussed later herein.

One of ordinary skill in the art will appreciate that the location, shape, depth, size and orientation of the aperture forming the first and second locking tab receivers 58 and 60 may vary, depending upon the clinical purpose, flow performance, dimensional size requirements of the cartridge insert and sealing surface requirements, and patient safety considerations for the body fluid cartridge exchange platform device 10. The shape of each receiver 58 and 60 can be a hole, depression, or ridge disposed into and/or through the wall surface of the platform housing 12 and can be made in a number of different configurations or geometric shapes including a circle, square, rectangle, crescent, or triangle. Further, each receiver 58 and 60 can be uniform, non-uniform, irregular, or formed into a desirable shape suitable for positive locking, containing, or anchoring the cartridge insert locking tab 62 into the wall of the platform housing 12. The receiver 58 and 60 must, however, be appropriately sized and dimensioned to receive, accommodate, and fix the radially extending locking tab 62 found on each of the tubular cartridge inserts 32 and 44, as will be discussed in further detail later herein.

Figure 3:
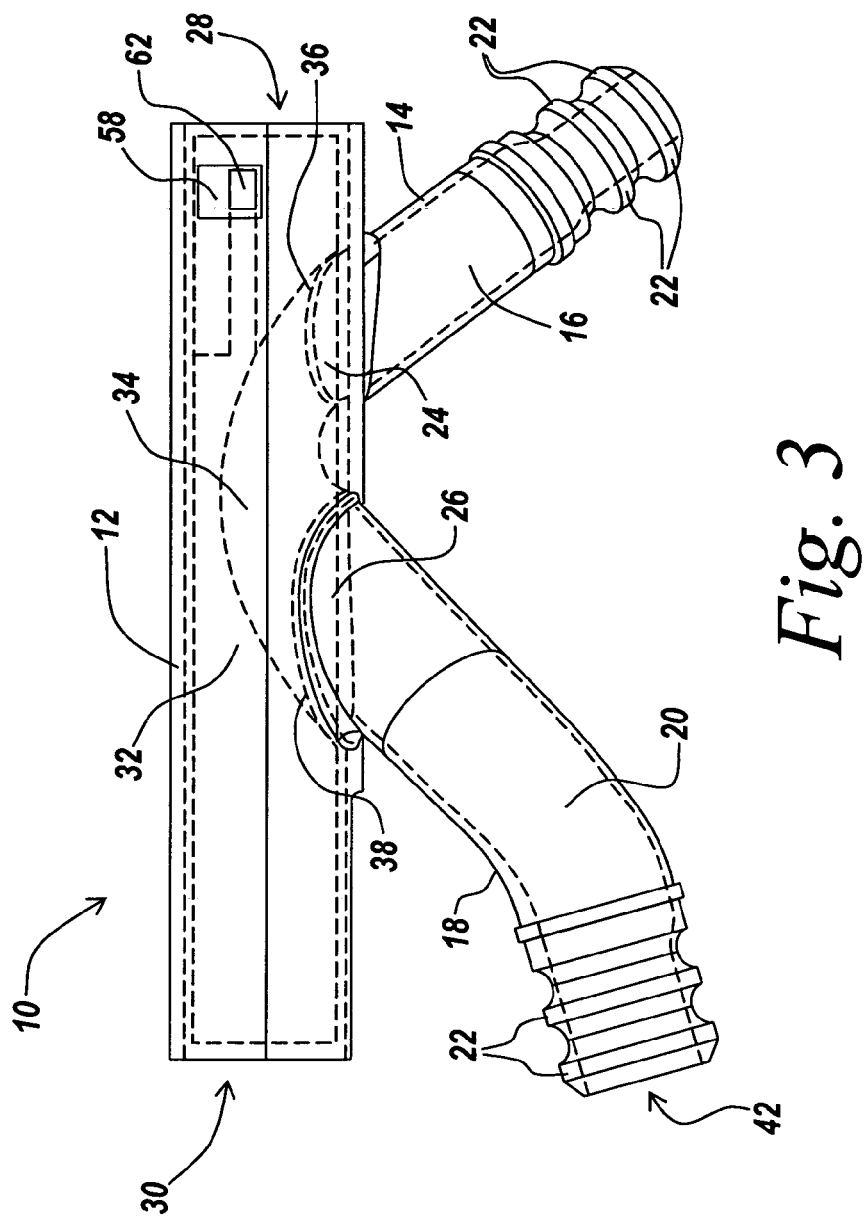
FIG. 3 is a diagrammatic illustration of the cartridge exchange platform device with one body fluid communicating cartridge installed within a hollow cartridge platform housing according to one embodiment of the present invention.

FIG. 3 provides visual detail of the fixed position of a primary body fluid cartridge insert (primary cartridge insert 32) contained entirely within the platform housing 12. The primary cartridge insert 32 contains an internal flow path 34 for body fluid or blood to enter, flow through, and exit, through the internal flow path 34 of the primary cartridge insert 32 when installed inside the cartridge exchange platform device 10. The installed primary cartridge insert 32 receives body fluid from the first leg member 14 and first internal passageway 16, and through the first leg member proximal port opening 24 of the platform housing 12. The internal flow path 34 inside the cartridge insert 32 completes a fluid circuit between the first and second leg member proximal port openings 24 and 26 of the cartridge exchange platform device 10 by coupling first and second sealing surface port openings 36 and 38 into alignment with the first and second leg member proximal port openings 24 and 26. The completion of the body fluid flow circuit between the first and second leg member internal passageways 16 and 20 of the cartridge exchange platform device 10, made possible by the internal flow path 34 of the primary cartridge insert 32, is required when a patient does not require the cartridge exchange platform device 10 to be connected to an external medical apparatus for treatment. The primary cartridge insert 32 is indicated for use when the patient does not require external connection or attachment to an external medical apparatus, and only needs circulating body fluid to flow continuously and unhindered through the internal flow path 34 and the first and second leg member internal passageways 16 and 20 of the cartridge exchange platform device 10. This arrangement allows the patient to perform their normal daily activities.

Figure 5A:
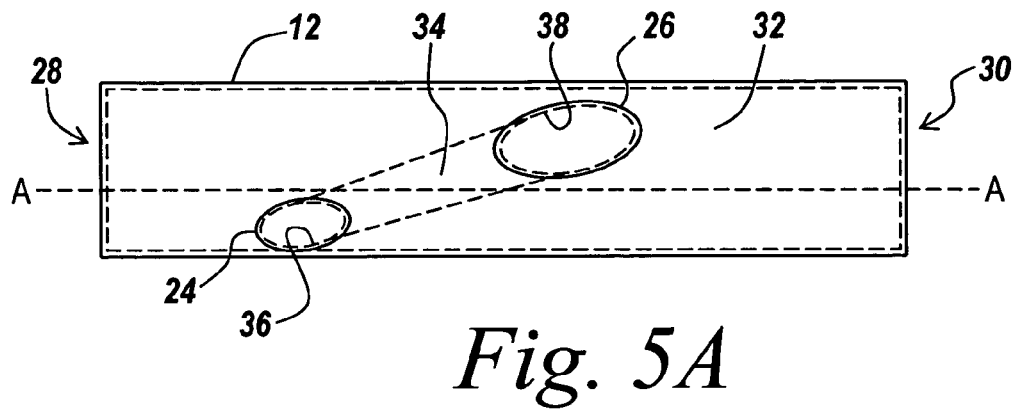
FIGS. 5A, 5B, and 5C are diagrammatic illustrations showing how hollow leg member port openings couple in alignment with matching first and second internal flow path port openings of an installed tubular cartridge insert, and how the port openings for each component can go into and out of flow path alignment during tubular cartridge insert movement, displacement, or exchange inside the hollow cartridge platform housing according one embodiment of the present invention.
Figure 5B:
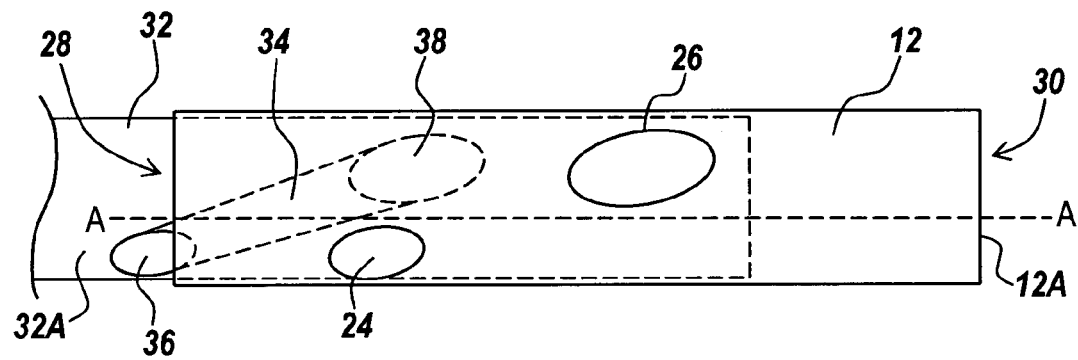
Figure 5C:
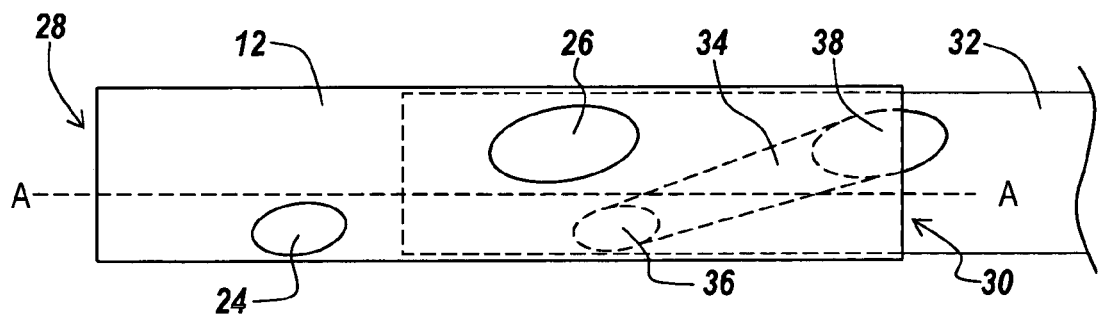

It should be noted that all internal body fluid flow path port openings, sealing surface port openings, and port opening alignment locations, including those of the first and second leg member proximal port openings 24 and 26 of the platform housing 12, are to couple and match the annular shape and size of those sealing surface port openings 36 and 38 of the cartridge insert 32, which complete the internal flow path 34 fluid circuit between the first and second leg member internal passageways 16 and 20, as illustrated in FIGS. 3 and 5A. The illustrations of FIGS. 5A, 5B, and 5C represent one example of many possible cartridge insert 32 sealing surface port opening alignment configurations that can be made to maximize flow performance, ensure manufacturability, and attain continuous body fluid utilization through the properly aligned cartridge insert 32 and sealing surface port openings 36 and 38 when coupled into alignment with those of the first and second leg member proximal port openings 24 and 26, located in the interior wall surface of the platform housing 12. FIG. 5B depicts the cartridge insert 32 being installed by forward directed movement from left to right, and through a first open end 28 of the platform housing 12. FIG. 5C shows the same cartridge insert 32 being displaced out through the second open end 30 of the platform housing 12 as shown in FIG. 5B, with the cartridge insert sealing surface port openings 36 and 38 going out from alignment with the first and second leg member proximal port openings of the platform housing 12 when a first cartridge insert 32 needed to be exchanged or removed out from the platform housing 12 by forward directed movement and contact from a second cartridge insert within the same platform housing 12.

The first leg member 14 includes the first hollow internal passageway 16 that provides fluid communication between the first leg member distal port opening 40, and the first leg member proximal port opening 24 located in the interior wall surface of the platform housing 12. The second hollow internal passageway 20 of the second leg member 18, and the second leg member proximal port opening 26 located in the interior wall surface of the platform housing 12 maintain fluid communication with the second leg member distal port opening 42. The primary cartridge or maintenance insert 32 includes the first sealable surface port opening 36 and a second sealable surface port opening 38, which communicate via the internal flow path, channel, or passageway 34 located internal to the cartridge insert 32 or made part of the outer sealing surface as an open channel. The first leg member proximal-port opening 24 aligns with the first cartridge insert sealing surface port opening 36. The second leg member proximal port opening 26 also aligns with the second cartridge insert sealing surface port opening 38 to complete the internal flow path circuit between the first leg member internal passageway 16, the second leg member internal passageway 20, and the primary cartridge insert 32 internal flow path, channel, or passageway 34.

A locking tab 62 extends in a generally outward and radial direction from the tubular form cartridge insert 32 into the first locking tab receiver 58 in the wall of the platform housing 12. The locking tab 62 disposes into the first receiver 58, thus causing the cartridge insert 32 to stop and become fixed in position within the platform housing 12. The locking tab 62 extends outward and generally beyond the outer radial sealing surface of the primary cartridge insert 32 to snap into place within the first receiver 58 when the primary cartridge insert 32 reaches its intended fixed destination within the platform housing 12. The locking tab 62 does not generally align the primary cartridge 32 within the platform housing 12, it merely prevents the installed primary cartridge insert 32 from further movement within the platform housing 12 once the installed primary insert reaches its intended fixed destination. The generally oval cross-sectional shape together with the tubular containment function of the platform housing 12 provides the radial alignment means for the first and second leg member proximal port openings 24 and 26 of the platform housing 12 with those sealing surface port openings 36 and 38 of the primary cartridge insert 32. The locking tab 62 serves the intended purpose to only stop, lock, or anchor the primary cartridge 32 at an intended fixed location when the primary cartridge 32 is properly disposed within the platform housing 12. The locking tab 62 is not part of any mechanical guidance or sealing surface feature within the tubular cartridge platform housing 12, nor does the locking tab 62 function as or perform a sealing surface purpose. Further, the locking tab 62 of the cartridge insert 32 is not part of any cartridge insert 32 installation guidance means, holding means, or holding element for the purposes of attaining sealing surface engagement between the cartridge insert 32 sealing surface 32A and the interior sealing surface 12A of the platform housing 12.

The cross-sectional area of the first internal passageway 16 of the first leg member 14 is less than the cross-sectional area of the second internal passageway 20 of the second leg member 18 in accordance with one embodiment of the present invention. The cross-sectional area of the first and second leg members 14 and 18 can vary, depending on the particular purpose, clinical application, anatomical location, fluid flow performance, or external medical treatment required of the cartridge exchange platform device 10.

The cartridge exchange platform device 10 illustrated in FIG. 3 is designed for use with any body fluid containing organ, including for use with a patient's arterial and venous blood vessels. The nominal blood fluid pressure, volume, and flow velocity through an artery is greater than the blood fluid pressure, volume, and flow velocity through a vein. The dimensional size ratio of the platform housing 12 and the first and second leg members 14 and 18, in addition to all internal fluid communicating cross-sectional areas of the first and second leg member internal passageways 16 and 20, can vary in diameter to each other to accommodate differences in fluid pressure and flow velocity gradients from a first fluid communicating organ to a second fluid communicating organ. For example, there exists a significant gradient difference between the nominal blood pressure, flow volume, and velocity of an artery, to that of the nominal blood pressure, flow volume, and velocity of a vein.

When the cartridge exchange platform device 10 is used as a means to provide an arterial to venous blood flow direction, more commonly referred in the healthcare industry as an AV shunt, or for the purpose of establishing a flow direction from a first higher pressure environment of the arterial blood system to a second lower pressure environment of the venous blood system, there can be a significant blood pressure gradient difference from the first leg member distal port opening 40 and first internal passageway 16, to the second leg member internal passageway 20 and second leg member distal port opening 42. One embodiment of the cartridge exchange platform device 10 includes a provision to keep the fluid pressure and flow rate exiting the second leg member distal port openings 42 located on the second leg member 18 generally less than the fluid pressure and flow rate entering the first leg member distal port opening 40. Likewise it can be desirable to make the fluid pressure and flow rate of the second leg member internal passageway 20 generally less than the fluid pressure and flow rate of the first leg member internal passageway 16. For this particular clinical purpose, the fluid pressure and flow rate gradient can be modulated by making the first leg member distal port opening 40 and first leg member internal passageway of the cartridge exchange platform device 10 smaller in cross-sectional area than the second leg member distal port opening 42 and first leg member internal passageway 20, and by making the first sealing surface port opening 36 on one end of the internal flow path 34 of the cartridge insert 32 smaller than the second sealing surface port opening 38 thereby allowing fluid to flow in a direction beginning from a first higher pressure and flow rate (e.g. higher blood pressure value) to a generally different or lower second pressure and flow rate (e.g. lower blood pressure value) as the fluid or blood flows through the cartridge exchange platform device 10.

For another clinical requirement, it may be desirable to reverse the flow direction and pressure gradient purpose of the body fluid cartridge exchange platform device 10, as previously described above, by increasing the forward directed flow rate and pressure out from the second leg member distal port opening 40 and second leg member internal flow path 16. For example, modulation of the first lower fluid pressure and flow rate to a second higher pressure and flow rate is accomplished by use of dimensionally reducing cross-sectional area flow path sections, or by use of multiple, progressively smaller flow path portions along the entire length of the forward directed flow path within the cartridge exchange platform device 10. Forward directed fluid flow can further be modulated from a first low fluid pressure value to a second higher fluid pressure value within the cartridge exchange platform device 10 by the use of a larger first leg member distal port opening 42, and larger first leg member internal passageway 20, than the smaller second leg member internal passageway 16, and smaller second leg member distal port opening 40.

Whether or not body fluid or blood traverses through the primary cartridge insert 32 and internal flow path 34 unhindered, or the body fluid or blood circulates out from the secondary cartridge insert 44 to an external fluid communicating medical apparatus through a first external port opening 50 in communication with an external flow path 51 and flows back again into the same cartridge insert 44 through a second external flow path 53 and through the second external port opening 48, the fluid pressure and flow rate within the cartridge exchange platform device 10 can be modulated, reduced, or increased by making the first internal passageway 16 cross-section area of the first leg member 14 different than the second internal passageway 20 cross-section area of the second leg member 18. For example, a larger second internal passageway 20 cross-sectional area than a first smaller internal passageway 16 causes the fluid pressure and flow gradient to lower from a first higher entering pressure and flow rate value as the body fluid traverses through the cartridge exchange platform device 10. Therefore, body fluid or blood pressure and flow rate through a cartridge exchange platform device 10 can be altered, changed, modulated, or decreased from a first higher entering pressure and flow rate value by making the second leg member internal passageway 20 larger or sufficiently different in cross-sectional area to the first leg member internal passageway 16. Such a fluid pressure and flow modulating feature is required for most arterial to venous body fluid communicating uses with the cartridge exchange platform device 10, where it would be desirable to reduce the higher arterial blood fluid pressure and flow rate value, down to a second more physiologic and generally lower fluid pressure and flow rate value, commensurate with that of the patient's ability to accommodate an elevated venous pressure and flow rate value that is less than the first higher arterial pressure and flow rate. For such clinical applications, purpose, and use of the cartridge exchange platform device 10, the fluid pressure and flow rate modulation feature helps minimize the damaging effects to circulating blood cells, blood platelets and or endothelial cell lined vein surfaces from exposure to nominal arterial blood pressure and flow rates encountered with more traditional arterial to venous body fluid connection means.

All tubular sealing surface engaging cartridge inserts of the cartridge exchange platform device 10, include one or more body fluid communicating internal flow paths, channels, or passageways 34 whose principal function is to complete a body fluid communicating circuit between the first leg member 14 and its internal passageway 16, through a portion of the platform housing 12, and through the second leg member 18 and its internal passageway 20. The cartridge insert internal flow path is generally tubular and can be further sized, dimensioned, or formed to either a conical or tapered shape, made generally smooth surfaced throughout, or made from several shorter faceted surfaces without sharp edges, and/or made coated, covered, or lined with medically purposeful bioactive substances (eg. such as an anticoagulant, antiseptic, gene therapy medication, anti-inflammatory medication, or a hydrophilic fluid surface treatment) to further reduce internal flow path fluid pressure resistance and flow rate resistance, internal flow path wall surface shear force, or to increase wall surface lubricity along all or a portion of the internal flow path or passageway 34, or to reduce the likelihood of circulating body fluid components and or blood cell components from being activated by direct surface contact with any portion of the internal flow path, channel or passageway 34 inside the primary cartridge insert 32, and including any portion of the external fluid communicating flow paths, channels or passageways 51 and 53 of the secondary cartridge insert 44. The coatings can be placed in all or part of the areas exposed to body fluids.

The generally tubular and arcuate internal flow path and flow surface characteristics of the internal flow path, channel, or passageway 34 located within the cartridge insert 32 and 44 carry throughout a wide variety of clinical purpose and indications for use, and further carry throughout the many possible tubular cartridge insert styles, types, and/or sealing surface configurations for use with the body fluid cartridge exchange platform device 10. The internal flow path, channel, or passageway 34 for any primary cartridge insert 32, including any secondary cartridge inserts 44 that employ an internal flow path, channel, or passageway 34 diagramed in FIG. 6, makes a slow, generally arcuate turn between the first sealing surface port opening 36 and the second sealing surface port opening 38 to maintain body fluid flow between the first leg member proximal port opening 24 and the first internal passageway 16 of the cartridge exchange platform device 10, to the second leg member proximal port opening 26 and second internal passageway 20. Sharp comers of less than 90 degrees or narrow cross-sectional area flow paths, channels or passageways are known by those of ordinary skill in the art to restrict or impede body fluid and blood flow, due to several different physical limiting flow conditions and or chemical variables that can coexist in the natural body fluid environment, e.g. body fluid viscosity, cellular component percentage of fluid volume, hematocrit, percentage of hydration and water content of the fluid contents, degree of systemic medication if applicable, coagulation, and or varying levels of body fluid toxicity as found in patients with ESRD.

The generally smooth, arcuate and angled turn of 90 degrees or greater within the internal flow path 34 of the cartridge insert 32 and 44 can be either continuous from the first annular sealing surface port opening 36 to the second annular sealing surface port opening 38, or can be made to function similar to an arcuate or angled turn by use of many smaller, non-continuous angles in sequence with many short, flat, or faceted surfaces, which when used as a whole contribute and function as a continuous arcuate internal flow path circuit between the first leg member 14 and internal passageway 16 and the second leg member 18 and internal passageway 20 within the cartridge exchange platform device 10. Such a generally smooth, arcuate radius and angled turn of 90 degrees or greater internal flow path function, plays a role in maintaining continuous body fluid and blood flow by minimizing body fluid stasis, pooling, and shear along the internal flow path 34 of the cartridge platform inserts 32 and 44. In addition, the lack of sharp, hard edge turns substantially prevents the occurrence of blood cells and or blood platelets from being damaged, activated or forced into aggregate bundle formation from direct contact with irregular shaped surfaces and sharp angled turns within the internal flow path, channel, or passageway 34.

The coupling means of the first and second leg members 14 and 18 to the platform housing 12 of the cartridge exchange platform device 10 has a generally smooth and aligned transition, such that the body fluid communicating internal flow path of the platform housing 12 and first and second leg member respective internal flow paths 16 and 20 do not have sharp, hard edged surfaces when coupled in alignment with the cartridge insert 32 and 44. The smooth first leg member internal passageway 16 coupling means to the platform housing 12 and the cartridge insert 32 or 44, and the smooth second leg member internal passageway 20 coupling means at different location to the same platform housing 12 wall surface and cartridge insert 32 or 44, further reduces the likelihood of bacterial colonization and bio-film formation from harboring into, aggregating on and anchoring to, uneven internal coupling surfaces in and around the tubular internal flow path portions of the platform housing 12, internal passageway portions 16 and 20 of the first and second leg members 14 and 18, and cartridge insert sealing surface port openings 36 and 38.

Figure 4:
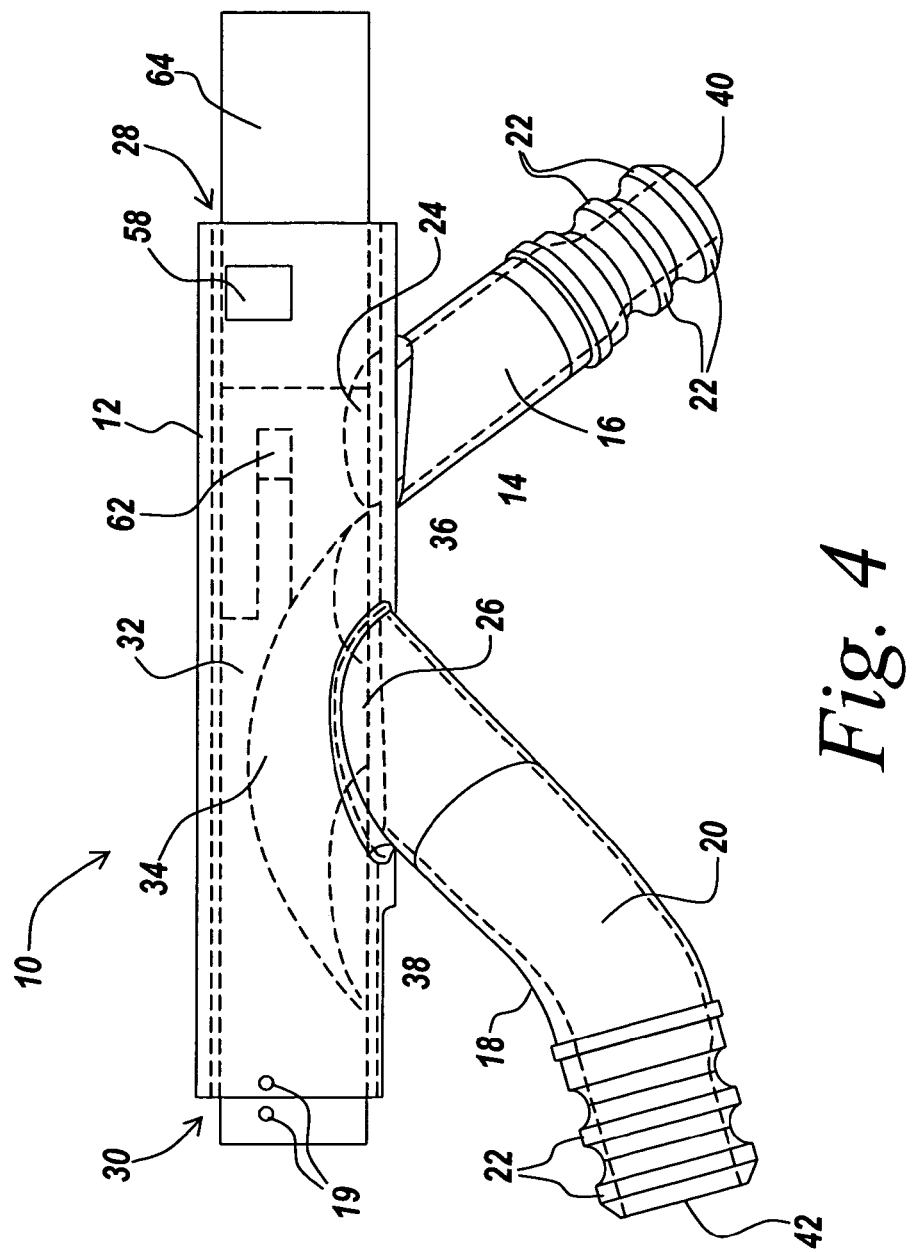
FIG. 4 is a diagrammatic illustration of the device with the cartridge insert of FIG. 3 in addition to a second or replacement cartridge insert displacing a first installed cartridge insert by forwarding direct contact and movement out one open end of the cartridge platform housing according to one embodiment of the present invention.

FIG. 4 illustrates the cartridge exchange platform device 10 with the primary cartridge insert 32 in a partially moved, displaced and un-fixed condition away from its intended fixed destination position within the platform housing 12. To exchange or remove a fixed or locked position cartridge insert 32 and 44 out from the inside of the platform housing 12, or any body fluid communicating cartridge insert installed in its intended operable and fixed position within the housing and having a locking tab 62, a user first must depress or push the locking tab 62 of the indwelling cartridge insert to be exchanged or removed, sufficiently inward through the first receiver 58 to release the locking tab from containment within the first receiver 58 and to subsequently allow the movement or displacement of the cartridge insert 32 or 44, by forcibly moving the now released cartridge insert out through one open end 28 or 30, of the platform housing 12. Once the locking tab 62 clears the containment means of the receiver 58 located in the wall of the platform housing 12, followed by simultaneous forward directed movement of the cartridge insert 32 by direct contact and displacement by another cartridge insert 44 away from its former fixed location within the platform housing 12, allows the locking tab 62 to remain in a generally recessed position inside the interior wall surface of the platform housing 12, until after the cartridge insert being exchanged, removed, or displaced by another or second cartridge insert 32 or 44, is completely expressed from the cartridge exchange platform device 10. It should be known that the cartridges 32 and 44 (see FIG. 6) illustrated herein are shown being inserted and removed from both the first platform housing opening 28 and the second platform housing opening 30 of the tubular cartridge exchange platform device 10. The cartridge insert examples illustrated in FIG. 6, and other body fluid communicating cartridge inserts not illustrated and made to work with the body fluid cartridge exchange platform device 10 in accordance with the present invention, can also be exchanged, inserted, installed into a fixed and operable position, and removed from the platform housing 12 using the same two annular platform housing openings 28 or 30 interchangeably.

As illustrated in FIG. 4, a second tubular cartridge insert 64 is shown partially entered into the platform housing 12 through the first platform housing tubular opening 28, with the first primary cartridge insert 32 being partially displaced out through the second platform housing tubular opening 30 by the user's forward directed movement of the second cartridge insert 64. To make ready the cartridge exchange platform device 10 prior to forward directed insertion of a new or second tubular cartridge insert 64 in through the first platform housing tubular opening 28, the user must first depress and hold the locking tab 62 of the first installed primary cartridge insert 32, so as to sufficiently release it from the locking tab receiver 58 in the wall of the platform housing 12 to allow forward directed movement of the primary cartridge insert away from its former fixed and locked position. To make ready the installation of the second cartridge insert 64, the locking tab 62 of the second tubular cartridge insert 64 must be recessed and held in a contained recessed condition prior to or simultaneous to the user's forward directed movement and insertion of the second cartridge insert 64 in through the first platform housing opening 28 and subsequent placement inside the tubular form platform housing 12. As part of any cartridge insert installation technique with a radially extending locking tab 62, the locking tab 62 must be held or sufficiently contained in an depressed condition to allow a portion of the locking tab 62 to enter into and make contact with the interior wall surface of the platform housing 12. By continued forward directed movement of the second tubular cartridge insert 64 within the platform housing 12 by the user, the un-fixed or released first primary cartridge insert 32 can then be expressed out through the cartridge platform housing second opening 30, as it is pushed outward by the user's continued forward directed movement of the second cartridge insert 64, and until the second cartridge insert reaches its intended fixed or locked destination within the cartridge exchange platform device 10.

Forward directed movement, insertion and removal of the cartridge inserts 32 and 44, in or out of the platform housing 12 is possible through either of the first and second platform housing openings 28 and 30. The cartridge insert 64 of this illustration is representative of any form of a tubular and locking tab cartridge insert that is made for bi-directional and forward directed insertion means by a user within a body fluid cartridge exchange platform device 10. Further, the cartridge insert 64 can be another alternative purposeful cartridge insert, such as another primary cartridge insert 32 or a secondary cartridge insert 44 with external body fluid communicating means out through one external cartridge insert non-sealing surface. The cartridge insert 32 and 44 and the platform housing 12 can each contain a marking 19 (see FIG. 4) acting as a direction indicator that indicates the correct arrangement and alignment for insertion of the insert 32 and 44 into the platform housing 12.

As the primary cartridge insert 32 is pushed forward from its former fixed and operable body fluid communicating position by direct contact and forward directed movement of the second cartridge insert 64 by the user, and moved simultaneously out through the second tubular platform housing opening 30, the first annular sealing surface port opening 36 and the second annular sealing surface 38 are both moved away from body fluid communication and or annular alignment with the first leg member proximal port opening 24 and the second leg member annular port opening 26 of the cartridge exchange platform device 10. In one embodiment of the invention, the interior wall surface distance between the first leg member proximal port opening 24 in the platform housing 12 and the first platform housing opening 28 must be greater than the diameter of the first internal flow path sealing surface port opening 36 of the cartridge insert 32. Likewise, the interior wall surface distance between the second leg member proximal port opening 26 in the platform housing 12 and the second platform housing opening 30 must be greater than the diameter of the second internal flow path sealing surface port opening 38 of the cartridge insert 32. The ratio of the interior wall surface distance between the first leg member proximal port opening 24 and the first platform housing opening 28 relative to the diameter of the first internal flow path sealing surface port opening 36 of the cartridge insert 32 must be greater than one. Likewise, the ratio of the interior wall surface distance between the second leg member proximal port opening 26 and the second platform housing opening 30 relative to the diameter of the second internal flow path sealing surface port opening 38 must also be greater than one. For example, if the desire is for the wall distance to be about 5% greater then the port diameter, the ratio would be greater than one, or 1.05. These two sealing surface distance ratios prevent body fluid from exiting out from the first and second leg member internal passageways 16 and 20 of the platform housing 12 during cartridge insert movement, displacement or exchange.

These dimensional sealing surface distance requirements also prevent large boluses of ambient air and/or continuous open air access from outside of the platform housing 12 from entering into the patient from either of the first leg member proximal port opening 24 and into the first leg member internal passageway 16, or the second leg member proximal port opening 26 and into the second leg member internal passageway 20 of the first and second leg members 14 and 18 during cartridge insert 32 and 44 movement by the user during insertion, exchange, or replacement. This patient safety feature reduces the likelihood of air and/or airborne contaminants from entering into body fluid circulation through the partially open and exposed second sealing surface port opening 38 as the cartridge insert 32 and the second sealing surface port opening 38 begins to exit and move outside of the platform housing 12 and the first sealing surface port opening 36 remains engaged to and inside the platform housing wall surface. The proper sealing surface distance prevents air from entering back into either the first and second leg member proximal port openings 24 and 26, and or from entering back into either the first and second leg member internal passageways 16 and 20 during cartridge insert 32 and 44 movement into or out from the cartridge exchange platform device 10. The sealing surface distance configuration of the cartridge exchange platform device 10 provides another patient safety feature as it also provides leak-proof exchange of the cartridge inserts 32 and 44 by not allowing body fluid or blood to escape out through or between the first or second leg member proximal port openings, or allow continuous flow of body fluid or blood to escape out from a partially displaced or partially exposed cartridge insert 32 with a portion of the internal flow path and one sealing surface port opening, either 36 or 38, partially exposed outside of the platform housing 12. The sealing surface distance safety design of this invention further reduces the likelihood of body fluid leaking out from inside the tubular cartridge exchange platform device 10 from between the engaged sealing surfaces of the platform housing 12 and the sealing surface of the inserted tubular cartridge insert 32 and 44, whether or not the cartridge inserts 32 and 44 are fixed into proper body fluid communication alignment within the platform housing 12, and whether or not the cartridge inserts 32 and 44 are in exchange transition partially into or partially out from a portion of the interior tubular wall surface of the platform housing 12.

This sealing surface design configuration of the cartridge inserts 32 and 44 can be further enhanced to prevent body fluid leakage out from between the cartridge insert sealing surface and the interior wall surface of the platform housing 12, by use of one or more thermoplastic elastomers on a portion of the tubular cartridge insert sealing surface, or by the use of one or more thermoplastic elastomers as a structural assembly component or part of the internal flow path sealing surface or port openings, located on the sealing surface of the tubular cartridge insert 32 or 44.

FIGS. 5A, 5B, and 5C, further illustrate an example of the first and second leg member proximal port opening 16 and 20 offset arrangement to each other and the offset port opening alignment relationship of the first and second sealing surface port openings 36 and 38 of the tubular cartridge insert 32. More specifically, if a line is drawn parallel to a center axis (axis A—A) of the interior lumen of the tubular platform housing 12 from the first platform housing opening 28 to the second platform housing opening 30, the line can pass between both the first leg member proximal port opening 24 and the second leg member proximal port opening 26, without intersecting either leg member proximal port opening 24 or 26. The line A—A represents the bi-directional movement path a tubular cartridge insert follows during insertion and removal from inside the tubular sealing surface of the platform housing 12. The offset position of the second leg member proximal port opening 26 relative to the first leg member proximal port opening 24 as shown, facilitates the insertion, exchange and removal of a sealably engaging tubular cartridge insert 32, containing one or more sealing surface port openings, without continuous leakage of body fluid between the interior wall surface of the cartridge exchange platform device 10.

FIG. 5B shows the primary cartridge insert 32 being removed through the first opening 28 of the platform housing 12. As the primary cartridge insert 32 moves out from inside of the platform housing 12, the second sealing surface port opening 38 is sufficiently offset such that it does not intersect with the first leg member proximal port opening 24 when the cartridge insert 32 is moved in either a forward or backward direction. Likewise, in FIG. 5C, the first sealing surface port opening 36 of the tubular cartridge insert 32 does not intersect with the second leg member proximal port opening 26 of the platform housing 12 as the primary cartridge insert 32 moves in or out through the second platform housing tubular opening 30.

Figure 6:
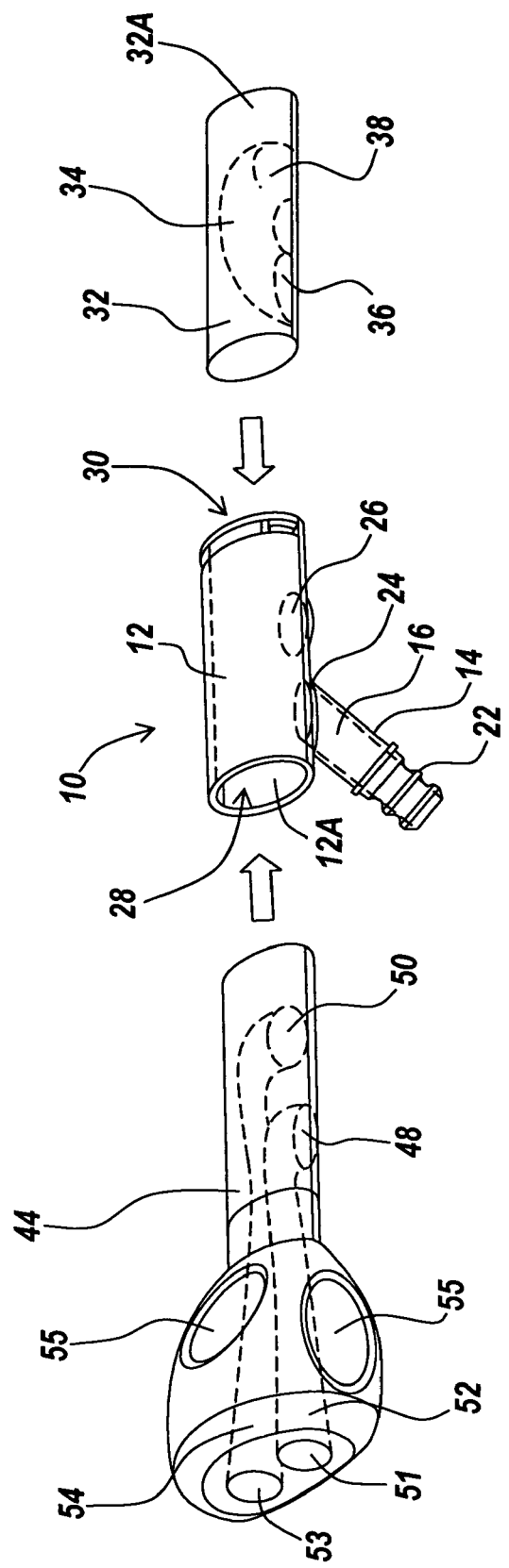
FIG. 6 is a perspective top view illustration of the hollow cartridge platform housing with two distinct cartridge insert examples that are bi-directionally insertable, removable, and interchangeable within the hollow cartridge platform housing according to one embodiment of the present invention.

The placement of the first and second leg member proximal port openings 24 and 26 relative to the first and second sealing surface port openings 36 and 38 of the primary cartridge insert 32 are also representative of the first and second leg member proximal port openings 24 and 26 relative to the first and second sealing surface port openings 48 and 50 of the secondary cartridge insert 44 (see FIG. 6). As either the primary cartridge insert 32 or the secondary cartridge insert 44 is pushed by the user into the interior lumen of the platform housing 12 of the cartridge exchange platform device 10, none of the internal flow path port openings located in the sealing surface of the cartridge insert (e.g., the first or second sealing surface port openings 36 or 38 in the tubular cartridge insert 32, or the first or second sealing surface port openings 48 or 50 in the secondary cartridge insert 44) pass over a leg member proximal port opening 24 or 26 inside the tubular platform housing other than the proper leg member proximal port opening with which it is designed to align and couple for completing body fluid communication between the first and second leg member internal passageways 16 and 20, once the cartridge insert 32 or 44 reach their intended fixed position within the cartridge exchange platform device 10.

FIG. 6 illustrates a perspective view of the minimally invasive cartridge exchange platform device 10 along with two examples of a body fluid communicating cartridge insert, a primary cartridge insert 32 for non-external body fluid communication and simple continuous fluid flow within the cartridge exchange platform device 10, and a secondary cartridge insert 44 for external body fluid communication out from the cartridge exchange platform device 10 via connection to any number of medical treatment devices. The platform housing 12 is shown in perspective view with the generally oval cross-section hollow interior. The first hollow leg member 14 is viewable from this perspective; however, the second hollow leg member 18 is substantially hidden behind the platform housing 12 of the cartridge exchange platform device 10. The first leg member proximal port opening 24 and the second leg member port opening 26 provide fluid communication into the interior wall surface inside the platform housing 12 lumen. The first leg member 14 includes a first internal passageway 16 and a distal port opening 40, and extends outward from the platform housing 12 and can be further oriented in a downward direction for a particular clinical purpose.

The secondary cartridge insert 44 is one example of an externally connectable device illustrated in FIG. 6. The particular secondary cartridge insert 44 illustrated is designed to provide external body fluid communication from a first leg member internal passageway 16 of the cartridge exchange platform device 10, through a first sealing surface external port opening 48 and external flow path 52, and then out through the first external port opening 51 of the secondary cartridge insert 44 to an externally connected medical treatment device. Following external treatment, body fluid is returned back into the secondary cartridge insert 44 through the second external port opening 53 and external flow path 54 and through the second sealing surface external port opening 50 of the secondary cartridge insert 44, and then into the second leg member internal passageway 20 of the cartridge exchange platform device 10. The external medical treatment device can be, for example, a dialysis machine 72 (see FIG. 8).

The secondary cartridge insert 44 has a cross-section generally compatible with the cross-section of the platform housing 12, which in the illustrated embodiment is generally oval. The secondary cartridge insert 44 includes a first sealing surface external port opening 48 and a second sealing surface external port opening 50 that communicate to a non-sealing external cartridge insert surface that is directed outward from the inside area of the platform housing 12 by one or more external passageways 51 and 53. The first sealing surface external port opening 48 facilitates body fluid communication with a first external passageway 52, while the second sealing surface external port opening 50 facilitates body fluid communication with a second external passageway 54. The secondary cartridge insert 44 additionally includes a first non-sealing surface external port opening 51 and a second non-sealing surface external port opening 53. The first and second external port openings 51 and 53 also provide fluid communication from outside the secondary cartridge insert 44 to an interior portion of the secondary cartridge insert 44. The first external passageway 52 communicates with the first external port opening 51 and to the first sealing surface external port opening 48. The second external passageway 54 communicates with the second external port opening 53 and to the second sealing surface external port opening 50.

To provide the patient external medical treatment access to internal body fluids with the cartridge exchange platform device 10 the secondary cartridge insert 44 is inserted into the interior portion of the platform housing 12 through the first platform housing opening 28 or the second platform housing opening 30, depending on the internal arrangement, alignment direction and or proper fluid communication orientation of the first sealing surface external port opening 48 and the second sealing surface external port opening 50 of the secondary cartridge insert 44. More specifically, if the secondary cartridge 44 sealing surface external port openings 48 and 50 are sized, dimensioned, shaped and disposed to smoothly couple with the first and second leg member proximal port openings 24 and 26 of the platform housing 12, upon insertion of the secondary cartridge insert 44 by the user through the first platform housing opening 28, then the secondary cartridge insert cannot be inserted through the second platform housing opening 30 of the cartridge exchange platform device 10 because the sealing surface port openings 48 and 50 would not align appropriately with the first and second leg member proximal port openings 24 and 26 inside the platform housing 12, thereby preventing internal body fluids from communicating outside of the cartridge exchange platform device 10. The secondary cartridge insert 44 is designed to prevent improper installation into the platform housing 12 by one externally disposed end being larger than the internal cross-section of the platform housing 12 and the platform housing openings 28 and 30, so that the proper insertion direction or the secondary cartridge insert 44 cannot be accidentally installed in a reversed or improper direction by the user and into the platform housing openings 28 or 30, or be inserted inappropriately from the proper direction it is designed to functionally align internally with, once installed inside the platform housing 12, without turning the secondary cartridge insert 44 around 180 degrees to fit the cartridge insert 44 into the platform housing 12. This change of direction of the secondary cartridge insert 44 would cause the first and second sealing surface port openings 48 and 50 to miss their intended alignment location with the first and second leg member proximal port openings 24 and 26 of the platform housing 12 because of the offset arrangement of the first and second leg member proximal port openings 24 and 26. If the secondary cartridge insert 44 did not have an externally disposed cartridge insert section or portion larger than the cross-section of the platform housing 12 first and second platform housing openings 28 and 30, the secondary cartridge insert 44 could be inserted incorrectly by the user through either the first or second platform housing openings 28 or 30.

The enlarged externally disposed section of the secondary cartridge insert 44 further serves to make the insertion and removal of the secondary cartridge insert 44 functionally easier to install by the user in a forward directed motion into the cartridge exchange platform device 10 by providing a larger tactile surface feature for the user to grasp and handle while working with the secondary cartridge insert 44. In addition, tactile ridges and or indentations 55 are provided on the larger externally disposed section of the secondary cartridge insert 44 for more secure gripping of the secondary cartridge insert 44 by the user. Such improvements can apply to any of the cartridge inserts used with the body fluid cartridge exchange platform device 10 of the present invention.

When the secondary cartridge insert 44 is installed in the proper insertion direction for first and second sealing surface external port opening 48 and 50 alignment into the platform housing 12 of the cartridge exchange platform device 10, the first sealing surface external port opening 48 comes into alignment with the first leg member proximal port opening 24 and the second sealing surface external port opening 50 comes into alignment with the second leg member proximal port opening 26. Once the secondary cartridge insert 44 reaches its fixed and intended position inside the platform housing 12, the secondary cartridge insert 44 facilitates body fluid communication between the first leg member 14 via the first leg member internal passageway 16 and the first leg member proximal port opening 24, through the first sealing surface external port opening 48 and external passageway 52, and to the first external port opening 51. Likewise, when the secondary cartridge insert 44 is positioned at its fixed intended position inside the platform housing 12, the coupled internal flow paths, channels or passageways of the cartridge exchange platform device 10 complete a fluid circuit arrangement within the secondary cartridge insert 44 and facilitate fluid communication between the second leg member 18 via the second leg member internal passageway 20 and the second leg member proximal port opening 26, through the second sealing surface external port opening 50 and external passageway 54, and to the second external port opening 53. The tubular secondary cartridge insert 44 sealably engages with a portion of the interior wall surface of the platform housing 12, hindering leakage of body fluids traversing through the external flow paths 52 and 54 of the secondary cartridge insert 44 and the cartridge exchange platform device 10. FIG. 8 further illustrates one example of implementation of the secondary cartridge insert 44 installed in an operable and fixed condition, inside the cartridge exchange platform device 10, for the purposes of providing internal body fluid communication with an externally connected medical treatment apparatus, e.g. a dialysis machine.

Another example of a tubular cartridge insert as illustrated in FIG. 6 is the primary cartridge insert 32. The primary cartridge insert 32 maintains a generally oval or elliptical cross-section profile that is compatible with the interior tubular cross-section profile of the platform housing 12 of the cartridge exchange platform device 10. The primary cartridge insert 32 includes a first sealing surface port opening 36 and a second sealing surface port opening 38. The primary cartridge insert 32 further includes an internal fluid communicating flow path, channel or passageway 34, between the first sealing surface port opening 36 and the second sealing surface port opening 38.

The primary cartridge insert 32 has a different user purpose than the secondary cartridge insert 44, and therefore the primary cartridge insert 32 has been designed to be properly installed into the platform housing 12 through either of the two housing platform openings, either through the first platform housing opening 28 or the second platform housing opening 30, interchangeably. Because the cross-section of the tubular form primary cartridge insert 32 is not greater dimensionally at any point than the cross-section of the platform housing 12 other than the depressible locking tab 62, which can extend radially out beyond the sealing surface if the cartridge insert 32, the previously discussed issue of not being able to use either platform housing opening 28 or 30 with the secondary cartridge insert 44 does not apply to the primary cartridge insert 32 or its use with the cartridge exchange platform device 10. The primary cartridge insert 32 is designed to be inserted bi-directionally through either the first or second platform housing openings 28 or 30 and when the primary cartridge insert 32 first and second sealing surface port openings 36 and 38 are oriented properly to align with the platform housing's first and second leg member proximal port openings 24 and 26.

As designed, the primary cartridge insert 32 sealably engages with a portion of the interior tubular wall surface of the platform housing 12 to ensure a leak-proof seal during insertion inside the cartridge exchange platform device 10. The primary cartridge insert 32 sealing surface engagement with the interior tubular wall surface of the platform housing 12 is made to prevent leakage of flowing body fluids out from the first and second leg members internal passageways 16 and 20 and respective proximal port openings 24 and 26 to the outside surface of the cartridge exchange platform device 10 during cartridge insert 32 movement, insertion, replacement or removal from the interior wall surface of the platform housing 12, or by forward directed movement and contact from a second cartridge insert 32 or 44 device inserted into the interior tubular wall surface of the platform housing 12. As the primary cartridge insert 32 is installed by the user by forward directed movement toward the intended fixed position within the cartridge exchange platform device 10, the first sealing surface port opening 36 of the primary cartridge insert 32 comes into fluid communication alignment with the first leg member proximal port opening 24 of the platform housing 12. Simultaneous to the same forward directed movement of the cartridge insert 32 toward the intended fixed position within the cartridge exchange platform device 10, the second sealing surface port opening 38 of the primary cartridge insert 32 comes into fluid communication alignment with the second leg member proximal port opening 26 cf the platform housing 12.

Once the cartridge insert 32 reaches its intended fixed position within interior tubular wall surface of the platform housing 12, the primary cartridge insert 32 first and second sealing surface port openings 36 and 38 couple in alignment with the first and second leg member proximal port openings 24 and 26 of the platform housing 12 to complete the body fluid communicating flow path inside the cartridge exchange platform device 10. The complete body fluid communicating flow path internal to the cartridge exchange platform device 10 established by proper installation and alignment of the cartridge insert 32 begins at the first leg member distal port opening 40 and continues through to the first leg member internal passageway 16 and proximal port opening 24 coupled in alignment with cartridge insert 32 first sealing surface port opening 36. The path further communicates through to the internal flow path 34 and second sealing surface port opening 38 coupled and aligned with the second leg member proximal port opening 26. The path further communicates through the second leg member internal passageway 20 and distal port opening 42 to complete the cartridge exchange platform device 10 internal fluid flow path.

One of ordinary skill in the art will understand and appreciate that the oval or elliptical cross-section illustrated for the tubular formed cartridge exchange platform device 10 and tubular formed cartridge inserts 32 and 44 can have many different annular cross-section profiles. For example, the elliptical cross-section profile of the platform housing 12 and the first and second platform housing openings 28 and 30 can be made non-elliptical by being formed into a circular, rectangular, square, triangular, or even non-uniform annular profile, such as an annular cross-section profile including notches, dimples, indentations, straight and curved portions, or the like. Each annular shape has benefits and disadvantages associated therewith. Any cartridge insert that is part of the complete body fluid communicating flow path inside the cartridge exchange platform device 10, such as the secondary cartridge insert 44 as one example, must have an annular cross-section profile to facilitate sealing engagement with a portion of interior tubular wall surface of the platform housing 12, following insertion of the secondary cartridge insert 44 into a portion of the hollow platform housing 12. The corresponding annular cross-section profile of a cartridge insert made part of the cartridge exchange platform device 10 does not need to be identical in cross-section shape or profile to the outer wall surface shape or profile of the platform housing 12, it need only be made sized to a dimension and cross-section profile in a manner to facilitate the sealing engagement of a portion of the cartridge insert 32 or 44 sealing surface to the interior wall surface of the platform housing 12 to hinder leakage of body fluids traversing through the cartridge exchange platform device 10.

The oval cross-section profile shown in the illustrated embodiments of the present invention aids in the proper alignment of cartridge inserts 32 or 44 that are inserted into the platform housing 12 of the cartridge exchange platform device 10, without sacrificing ease of cartridge insert exchange. The elliptical tubular surface inside of the oval platform housing 12 avoids the existence of interior corners, which are more difficult to attain cartridge insert 32 or 44 sealing surface engagement and sealing surface port opening 36 and 38 alignment with the first and second leg member proximal port openings 24 and 26 in the interior wall surface of the platform housing 12 to prevent flowing or continuous body fluid leakage from occurring during cartridge insert 32 or 44 exchange, and to further maintain an easy to clean interior wall surface environment inside the oval cartridge exchange platform device 10. The oval shape also allows any cartridge insert that is made part of the body fluid cartridge exchange platform invention having the corresponding oval profile cross-section to be inserted in only one of two positions, a first position and a second position 180 degrees in rotation from the first position. It is not possible to insert a cartridge insert having a corresponding oval profile in a manner where it is miss-aligned by a partial rotation between 0 and 180 degrees. Other different cross-section profile shapes can incorporate this annular alignment feature, however it is not necessary for operation of the present invention, so long as a portion of the inserted cartridge insert 32 and 44 of the cartridge exchange platform device 10 is appropriately oriented to provide body fluid communication upon insertion to its corresponding fixed and intended position within the cartridge exchange platform device 10, as described herein. The oval cross-section profile additionally provides sufficient sealing surface volume and radial surface area width to maximize offset placement of the first and second leg member proximal port openings 24 and 26 inside the platform housing 12 in the smallest cross-sectional area suitable for maximizing the arcuate internal flow path cross-section area inside the internal flow path 34 of the cartridge insert 32 for body fluid to uniformly traverse and flow through the cartridge exchange platform device 10.

FIG. 7 further illustrates two different examples of possible purpose cartridge inserts having either internal or external fluid communicating flow paths, channels, or passageways made to function and sealably engage with the hollow cartridge platform housing 12 as shown in the perspective illustration of FIG. 6 from a viewpoint underneath the body fluid cartridge exchange platform device 10. As can be seen in FIG. 7, the primary cartridge insert 32 is sized, shaped, and dimensioned to fit within the first or second openings 28 or 30 of the hollow cartridge platform housing 12. Once the primary cartridge insert 32 is inserted and installed into its intended fixed position within the hollow cartridge platform housing 12 by moving the primary cartridge insert 32 from left to right into the first opening 30, the first sealing surface port opening 36 and the second sealing surface port opening 38 of the primary cartridge insert 32 align with and couple to the first leg member proximal port opening 24 of the first leg member 14. This occurs generally contemporaneously with the alignment with and coupling to the second leg member proximal port opening 26 of the second leg member 18 of the hollow cartridge platform housing 12. Thus, a complete body fluid communicating flow path is formed inside the body fluid cartridge exchange platform device 10 originating from the first leg member distal port opening 40 of the first leg member 14, through the corresponding internal passageway 16, through the internal flow path 34 of the primary cartridge insert 32, through the second leg member internal passageway 20 of the second leg member 18, and out through the second leg member distal port opening 42. This fluid communicating flow path direction is reversible from the second leg member 18 to the first leg member 14 of the hollow cartridge platform housing 12, depending on the clinical requirements of the patient and desired direction of body fluid flow through the body fluid cartridge exchange platform device 10.

When the patient requires use of the secondary cartridge insert 44 for external body fluid communication for medical treatment with the body fluid cartridge exchange platform device 10, the secondary cartridge insert 44 as illustrated in FIG. 7 is inserted by forward directed movement into the second opening 30 of the hollow cartridge platform housing 12 by forward directed contact and displacement of the primary cartridge insert 32 following release of any locking tab engagement within the hollow cartridge platform housing 12 by the user. As the secondary cartridge insert 44 is moved into its intended fixed position within the hollow cartridge platform housing 12, the first sealing surface external port opening 48 and the second sealing surface external port opening 50 come into body fluid communication alignment with the first leg member proximal port opening 24 of the first leg member 14 and second leg member internal passageway 1, generally simultaneous to the second leg member proximal port opening 26 of the second leg member 18 and corresponding internal passageway 20 of the cartridge platform housing 12. Once the secondary cartridge insert 44 is installed to its intended fixed position, the first leg member internal passageway 16 aligns to form an external body fluid communication flow path with the first external flow path, channel, or passageway 52 and the first non-sealing surface external port opening 51 of the secondary cartridge insert 44. Likewise, the second leg member internal passageway 20 of the hollow cartridge platform housing 20 aligns to form an external body fluid communication flow path with the second external flow path, channel, or passageway 54 and the second non-sealing surface external port opening 53 of the of the secondary cartridge insert 44.

When the primary cartridge insert 32 is fully installed or inserted by the user to its fixed and operable destination within the hollow cartridge platform housing 12, the internal flow path, channel, or passageway 34 of the cartridge insert 32 provides a body fluid communicating circuit between the first leg member 14 and corresponding internal passageway 16 with the second leg member 18 and corresponding internal passageway 20 inside the body fluid cartridge exchange platform device 10. Therefore, any body fluid, including blood that flows through and/or communicates with the first leg member 14 and first leg member internal passageway 16, must also communicate with and/or flow through the internal flow path, channel, or passageway 34 of the primary cartridge insert 32 and further flow through and/or communicate with the second leg member 18 and second leg member internal passageway 20 of the body fluid cartridge exchange platform device 10. Thus, for example, the first leg member 14 can communicate with an artery or first body fluid organ within a patient, and the second leg member 18 can communicate with a vein or second body fluid organ within the patient. In such an arrangement, the body fluid or blood communicates with or flows through the first internal passageway 16 of the first leg member 14, and must communicate with or flow through the internal flow path, channel, or passageway 34 of the primary cartridge insert 32, and further flow through and or communicate with the second leg member 18 and second leg member internal passageway 20, and into the vein or second body fluid organ within the patient. The primary cartridge insert 32 as a component of the body fluid cartridge exchange platform device 10 is therefore a continuous body fluid organ communicating cartridge insert for medical use with one or more internal body fluid organs during periods of time when the patient does not require external body fluid communication and connection to any number of external medical treatment devices.

When the secondary cartridge insert 44 is installed inside the hollow cartridge platform housing 12 to its fixed and intended operable position, a different body fluid communicating arrangement and/or flow path configuration is created between the first and second leg members 14 and 18 by the secondary cartridge insert 44 inside the body fluid cartridge exchange platform device 10 than the body fluid communicating arrangement and/or internal flow path of the primary cartridge insert 32. If, for example, the first leg member 14 communicates with an artery of the patient and the second leg member 18 communicates with a vein of the patient, the flow path and fluid direction of the blood traverses the first internal passageway 16 of the first leg member 14 toward the second internal passageway 20 of the second leg member 18 by completion of a fluid circuit within the platform housing 12 by an installed cartridge insert 32. However, with the secondary cartridge insert 44 installed inside the platform housing 12, the body fluid or blood traverses from the first internal passageway 16 of the first leg member 14 and into the first external flow path 52 of the secondary cartridge insert 44. Such a body fluid communicating arrangement or flow path configuration made by the installation of the secondary cartridge insert 44 inside the hollow cartridge platform housing 12 allows the body fluid to exit through and communicate with the first non-sealing external surface port opening 51 to whatever external medical treatment method or device the secondary cartridge insert 44 is connected. When the connected external medical treatment device returns the body fluid back through the second non-sealing surface external port opening 53 and into the external flow path 54 of the secondary cartridge insert 44, fluid flow continues out through the second sealing surface external port opening 50, into the second leg member proximal port opening 26 and into the second internal passageway 20 of the second leg member 18. Therefore, the body fluid or blood flow supplied from the first and second leg members 14 and 18 of the body fluid cartridge exchange platform device 10, that communicates with and traverses through and installed secondary cartridge insert 44, undergoes a different body fluid communicating flow circuit and external flow path configuration when required by the patient for external medical treatment, e.g., dialysis.

FIG. 8 provides a detailed illustration of one example of how body fluid cartridge exchange platform device 10 is implanted percutaneously through the skin utilizing minimally invasive surgical techniques to an arm 78 of a patient in accordance with the teachings of the present invention. A portion of the small diameter first leg member 14 and a portion of the small diameter second leg member 18 of the body fluid cartridge exchange platform device 10 penetrate through the skin of the arm 78 of the patient. As can be seen, the limited amount of surface area surrounding each leg member 14 and 18 that makes physical contact with the topical skin surface and further requires wound healing after implantation of the body fluid cartridge exchange platform device 10 is substantially smaller than a surface area surrounding the main body platform housing 12 of the body fluid cartridge exchange platform device 10. In addition, placement of the first percutaneous wound in the patient's arm 78 for a portion of the first leg member 14 at a separate or distal location from the second percutaneous wound of a portion of the second leg member 18 and further separated by a distance or section of healthy, non-surgically effected, skin tissue, such that if the first percutaneous wound becomes topically infected, there is a significantly smaller likelihood of the infection spreading to the second percutaneous wound.

As illustrated in FIG. 8, the surgically installed body fluid cartridge exchange platform device 10 demonstrates one example of how a portion of the first leg member 14 couples subcutaneously with a first organ communicating means 84, while a portion of the second leg member 18 couples with a second organ communicating means 86 below the epidermis of the patient's arm 78. The first and second organ communicating means 84 and 86 can have many different connection and attachment mechanisms, synthetic vascular graft and suture material, rare earth or allow metal material, natural tissue, and/or medical grade plastic tubing suitable for implantation. The first organ communicating means 84 couples with a first body fluid organ 80 of the patient, while the second organ communicating means 86 further couples with a second body fluid organ 82 of the patient. In another embodiment of the invention, the first organ communicating means 84 couples to the first body fluid organ 80 and the second organ communicating means further couples to the same first body fluid organ 80.

As further illustrated in FIG. 8, the majority of the external surface area of the body fluid cartridge exchange platform device 10 resides above the skin of the patient following implantation and is shown with the secondary exchange cartridge insert 44 installed into the body fluid cartridge exchange platform device 10 and connected to an external medical treatment apparatus 72 via connected medical treatment tubes 74 and 76. A first medical treatment tube 74 couples with the first non-sealing surface external port opening 51 and a second medical treatment tube 76 couples with the second non-sealing surface external port opening 52 to provide body fluid communication external to the secondary exchange cartridge insert 44 from inside the body fluid cartridge exchange platform device 10. The first and second medical treatment tubes 74 and 76 additionally couple with the external medical treatment apparatus 72, which is a dialysis machine in the illustrated embodiment. One of ordinary skill in the art will appreciate that the dialysis machine is merely one example of an external medical apparatus 72 that can make use of the body fluid cartridge exchange platform device 10 of the present invention. Other medical treatment devices that can be used with the body fluid cartridge exchange platform device 10 include devices for delivering medication, devices for delivering nourishment, devices for temperature regulation and oxygenation, and devices for invasively monitoring body fluid content and/or function.

In operation, the body fluid or blood flows from the body fluid organ or artery 80, through the first organ communicating means 84 and the first internal passageway 16 of the first leg member 14, and out through the first external flow path 52 of the secondary exchange cartridge insert 44. The secondary exchange cartridge insert 44 then directs the body fluid or blood flow out through the first non-sealing surface external port opening 51, through the first medical treatment tube 74, and to the dialysis machine 72. The dialysis machine 72 filters the blood, and returns it back to the secondary exchange cartridge insert 44 through the second medical treatment tube 76 and into the second non-sealing surface external port opening 53. The secondary exchange cartridge insert 44 receives the returning blood through the second external flow path 54 and then directs the blood out of the secondary cartridge insert 44 and into the second internal passageway 20 of the second leg member 18 of the body fluid cartridge exchange platform device 10, through the second organ communicating means 86, and into the second body fluid organ or vein 82 of the patient. When dialysis treatment is complete, the first and second medical treatment tubes 74 and 76 are clamped off and disconnected from the dialysis machine so that the user can then remove and exchange the secondary cartridge insert 44 by insertion of the primary cartridge 32 to resume circulation of the blood flow from the body fluid organ or artery 80 directly to the vein 82 when the patient no longer requires connection to external medical treatment.

Figure 9A:
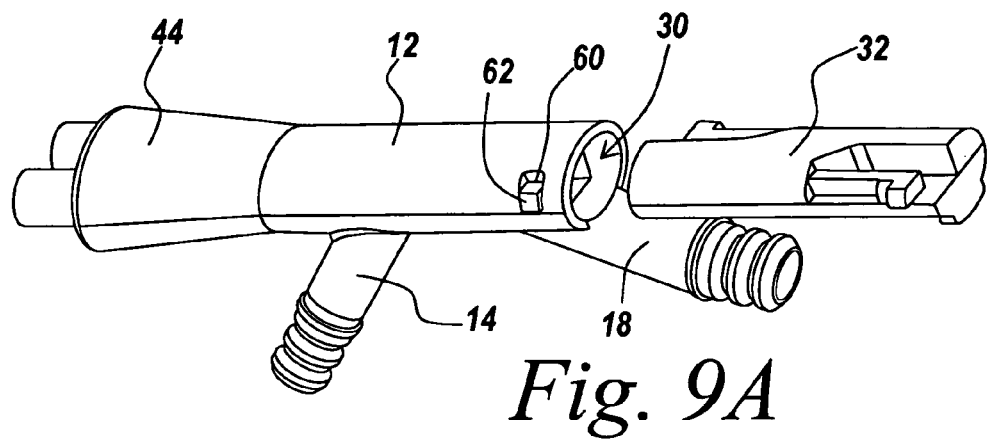
FIGS. 9A, 9B, and 9C are perspective illustrations of one example of a hollow cartridge platform housing with one or more cartridge insert tab receiver elements, and two interchangeable cartridge insert examples with one or more positively locking tab features, which snap into the hollow cartridge platform housing insert tab receiver elements after complete cartridge installation within the hollow cartridge platform housing according to one embodiment of the present invention.
Figure 9B:
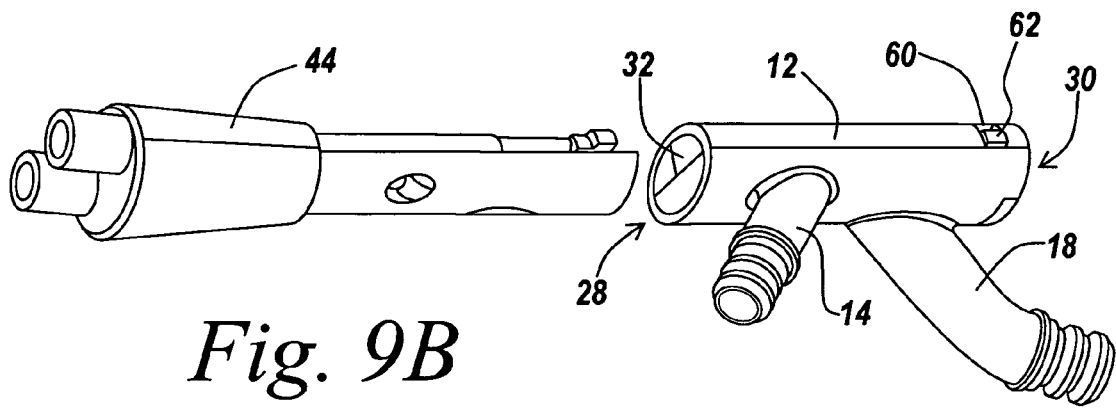
Figure 9C:
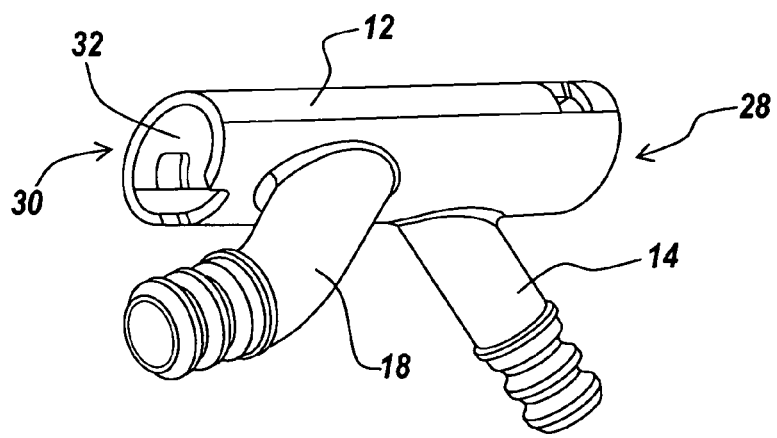

FIGS. 9A, 9B, and 9C show two examples of the various cartridge inserts that can be installed into the hollow cartridge platform housing 12 in a manner illustrating the swapping or bi-directional exchange of one cartridge insert for another. FIG. 9A begins with the secondary exchange cartridge insert 44 installed and locked within the hollow cartridge platform housing 12. The primary cartridge insert 32 is positioned to enter the hollow cartridge platform housing 12 through the second opening 30. As this occurs, the user depresses the locking tab 62 of the indwelling secondary cartridge insert 44 through the second receiver 60 in the wall of the hollow cartridge platform housing 12, so that the primary cartridge insert 32 can be pushed in a forward directed motion to push and/or displace the secondary cartridge insert 44 out through the first platform housing opening 28 of the body fluid cartridge exchange platform device 10. FIG. 9B illustrates the secondary cartridge insert 44 having been removed from the hollow cartridge platform housing 12, while the primary cartridge insert 32 is resident within the internal hollow portion of the hollow cartridge platform housing 12, and the locking tab 62 is in place within the second receiver 60. FIG. 9C illustrates a perspective view of the primary cartridge insert 32 contained and locked in place within the hollow structure of the hollow cartridge platform housing 12. The progression illustrated in FIGS. 9A, 9B, and 9C is reversible in that with the primary cartridge insert 32 installed, the secondary cartridge insert 44 can be inserted in the second housing opening 30 to push and displace the primary cartridge insert 32 out of the hollow cartridge platform housing 12 through the first housing opening 28, provided the locking tab 62 is depressed sufficiently to allow the primary cartridge insert 32 to be released and moved by direct contact with the secondary cartridge insert 44.

Figure 10A:
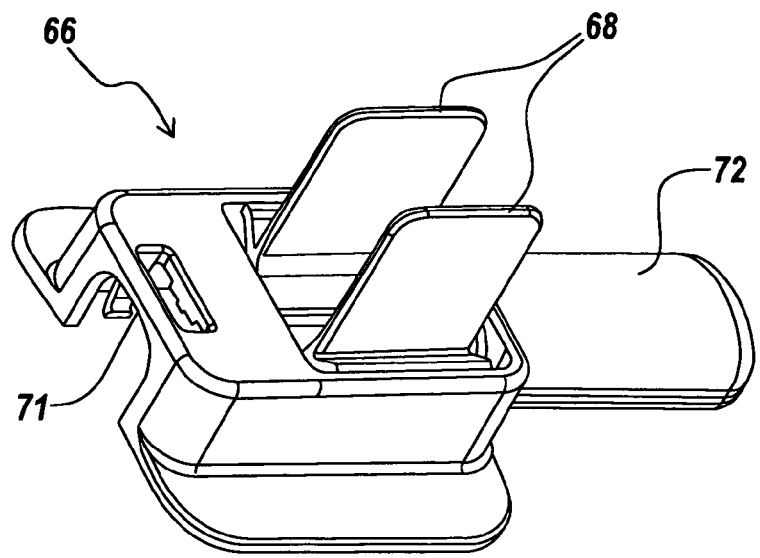
FIGS. 10A and 10B are perspective top and bottom view illustrations of a cartridge insert exchange tool with a closed containment chamber on one end of the exchange tool to receive, house, and contain an expressed or removed cartridge insert according to one aspect of the present invention.
Figure 10B:
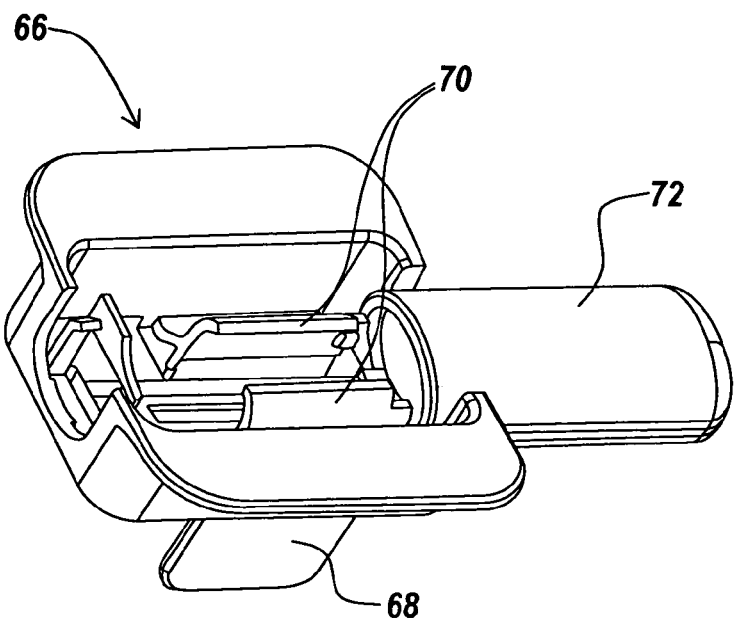

FIGS. 10A and 10B illustrate an example of a cartridge insert exchange tool 66 for exchanging cartridge inserts within the hollow cartridge platform housing 12. The cartridge insert exchange tool 66 includes a set of grips 68 that are pinched together by the user to allow a clamp 70 to fit over a portion of the hollow cartridge platform housing 12. Once the cartridge insert exchange tool 66 is positioned on top of the hollow cartridge platform housing 12, the grips 68 are related by the user to allow the clamp 70 to attach to, and enclose, a portion of the hollow cartridge platform housing 12. A portion of the hinged clamp is made to come into direct contact with a portion of the indwelling locking tab 62 contained within the second receiver 60 upon enclosure of the hollow cartridge platform housing 12 by the insert exchange tool 66 to depress the locking tab 62 to facilitate its release and subsequent cartridge insert exchange. As a cartridge insert 72 exits the hollow cartridge platform housing 12 by the forward directed movement of a second cartridge insert, the first cartridge insert 72 enters an expired insert containment chamber located within an internal portion of the insert exchange tool 66. Once the expired first cartridge insert 72 has been completely displaced and removed from the hollow cartridge platform housing 12 and contained in place within the containment chamber of the insert exchange tool 66, the user pinches the grips 68 to release the clamp 70 from the hollow cartridge platform housing 12 to allow the user to lift and remove the insert exchange tool 66 from the body fluid cartridge exchange platform device 10 for subsequent disposal.

To aid in the insertion and removal of cartridge inserts, the cartridge insert exchange tool 66 can also contain a marking 71 acting as a direction indicator. The marking 71 indicates the correct arrangement and alignment for insertion of the first cartridge insert 72 into the platform housing 12. The location of the marking 71 on the cartridge insert exchange tool 66 can vary to maximize its usefulness and the ability of a user to see the marking 71.

The primary cartridge insert 32 and the secondary cartridge insert 44 are merely two possible cartridge insert configurations made possible for use in conjunction with the present invention. It is anticipated that a number of different cartridge insert purposes will require different body fluid communication geometries and configurations, which can be utilized in conjunction with the body fluid cartridge exchange platform device 10 of the present invention.

The leg members 14 and 16 of the present invention as disclosed herein facilitate the majority of the externally cleanable surface area and all cartridge insert physical exchange areas of the hollow cartridge platform housing 12 remaining external to the body of the patient, while only portions of the leg members and 14 and 18 penetrate the skin of the patient for body fluid communication with internal organs. This external body fluid cartridge exchange platform device 10 of the present invention reduces the potential contact and source of infection complications that can come from direct topical skin contact with the moving parts of the body fluid communicating cartridge inserts and the hollow cartridge platform housing openings, which facilitate external to the body cartridge insert exchange. This minimally invasive percutaneous implant device also reduces pain and touch sensitivity to handling or manipulation of the hollow cartridge platform housing or cartridge inserts during insertion and removal of the cartridge inserts and connection to external medical treatment devices. The raised hollow cartridge platform housing is placed substantially horizontal to the skin surface, providing space underneath the raised platform of the hollow cartridge platform housing for natural movement of the skin and/or moderate movement of the body fluid cartridge exchange platform device from side to side, in addition to providing adequate access for hygienic care of the patient's skin around the percutaneous leg members. The ability to make the raised platform hollow cartridge platform housing and corresponding cartridge inserts and engageable sealable surfaces all tubular, facilitates the exchange of cartridge inserts with a simplified bi-directional arrangement. The sealing surface distance between the end openings of the hollow cartridge platform housing and the sealing surface port openings inside the tubular platform housing, which communicate with the internal body fluid passageways creates a leak proof cartridge insert method to install and/or exchange one cartridge insert for another without loss of body fluids or infiltration of airborne particles to the internal flow paths, channels, or passageways inside the body fluid cartridge exchange platform device. Changeable cartridge inserts can be sealably contained within the hollow cartridge platform housing by making the external portion of the raised platform hollow cartridge platform housing open at each end for bi-directional insertion and/or exchange of different cartridge inserts. The incorporation of one or more internal flow paths, channels, or passageways in the body fluid cartridge exchange platform device that communicate directly to and connect with external devices provides safe and simplified external access to the internal body fluid organs of a patient for medical, diagnostic, or therapeutic purposes.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

What is claimed is:

1. A body fluid cartridge exchange platform device, comprising:
   a tubular cartridge insert and
   a hollow tubular platform housing having a generally oval cross-section, a first end with a first opening and a second end with a second opening, wherein said first opening and said second opening facilitate insertion of said tubular cartridge insert that sealably engages inside the platform housing, and said first opening and said second opening facilitate bi-directional installation through either of said first opening and said second opening and bi-directional removal of said tubular cartridge insert through either of said first opening and said second opening regardless of which opening said tubular cartridge insert was installed through.

2. The device of claim 1, further comprising a small diameter first hollow leg member having an internal diameter, the leg member suitable for extending from the platform housing through skin of a patient for facilitating body fluid communication between an organ and at least a portion of the platform housing and tubular cartridge insert.

3. The device of claim 2, wherein the first hollow leg member supports the platform housing removed from the skin of the patient.

4. The device of claim 2, wherein the tubular cartridge insert provides a substantially arcuate flow path through the platform housing.

5. The device of claim 2 further comprising a second hollow leg member extending from the platform housing and penetrating through the skin of the patient and completing a fluid communication flow path extending between the first hollow leg member and the second hollow leg member through the tubular cartridge insert.

6. The device of claim 5, wherein the first and second hollow leg members include multiple internal lumens that communicate with the platform housing.

7. The device of claim 6, wherein the multiple internal lumens are adapted to communicate with multiple organs.

8. The device of claim 7, further comprising an external communicating passageway coupled to one of the openings of the platform housing and adapted to provide communication between the organ and an external destination.

9. The device of claim 8, wherein the external destination is adapted to provide a mechanism of drug delivery to supply one or more drugs to the organ.

10. The device of claim 5, wherein the first and second hollow leg members have a diameter of less than about 10 mm.

11. The device of claim 5, wherein the first and second hollow leg members each further comprise a microporous cell penetrable cuff disposed at a sub-dermal end of the first and second hollow leg members when implanted in a patient.

12. The device of claim 5, further comprising a bioactive coating disposed on at least a portion of the flow path between the first hollow leg member and the second hollow leg member through the tubular cartridge insert.

13. The device of claim 2, wherein the tubular cartridge insert provides a flow path through the platform housing and wherein the flow path has a diameter varying from a diameter relatively greater than an internal diameter of the first hollow leg member to substantially a same diameter as the internal diameter of the first hollow leg member.

14. The device of claim 2, wherein multiple tubular cartridge inserts are sealably engaged within the platform housing in alignment and communicate with the leg member.

15. The device of claim 1, wherein the tubular cartridge insert includes a locking mechanism for locking the tubular cartridge insert into a desired alignment within the platform housing.

16. The device of claim 15, wherein the locking mechanism is a flexible tab that extends from the tubular cartridge insert.

17. The device of claim 16, wherein the platform housing includes a receiver for receiving the flexible tab to hold the tubular cartridge insert in a desired alignment.

18. The device of claim 1, further comprising at least one marking disposed on at least one of the tubular cartridge insert and the platform housing that is suitable as an insertion direction indicator for the tubular cartridge insert.

19. An access device for providing access to internal organs, comprising:
a housing having a generally oval cross-section, a first opening at a first end and a second opening at a second end; and
a cartridge suitable for sealingly engaging an interior of the housing, the cartridge being insertable through either of the first opening and the second opening and removable through either of the first and second openings regardless of which opening the cartridge was inserted through.

20. The device according to claim 19, further comprising a first port and a second port disposed through a wall of the housing.

21. The device according to claim 20, further comprising a first leg having at least a first passage in communication with the first port and a second leg having at least a second passage in communication with the second port.

22. The device according to claim 21, wherein the first leg extends in a staggered and divergent manner from the second extending leg along the wall of the housing.

23. The device according to claim 21, further comprising a channel disposed within the cartridge.

24. The device according to claim 23, wherein the channel completes a flow path between the first passage and the second passage through the first and second ports.

25. The device according to claim 24, further comprising at least one external passage in communication with the channel of the cartridge, the external passage being suitable for at least one of introducing and removing a substance.

26. The device according to claim 24, further comprising a first channel port and a second channel port at opposite ends of the channel within the cartridge.

27. The device according to claim 26, wherein a distance between the first channel port and a first end of the cartridge is greater than a diameter of the first channel port.

28. The device according to claim 27, wherein a distance between the second channel port and a second end of the cartridge is greater than a diameter of the second channel port.

29. The device according to claim 24, further comprising a bioactive coating disposed on at least a portion of the flow path.

30. The device according to claim 21, wherein the first and second legs are configured to penetrate skin of a patient.

31. The device according to claim 21, wherein the first and second legs are configured to support the housing distally from a surface of skin of a patient.

32. The device according to claim 21, wherein the first and second legs are minimally invasive when implanted in a patient.

33. The device according to claim 21, wherein the first and second legs each have an outer diameter of less than about 10 mm.

34. The device according to claim 21, wherein the first and second legs further comprise a microporous cell penetrable cuff for sub-dermally anchoring the first and second legs below a skin surface of a patient.

35. The device according to claim 21, wherein the first passage of the first leg and the second passage of the second leg are configured to be placed in fluid communication with the organs.

36. The device according to claim 19, wherein the housing is generally tubular.

37. The device according to claim 19, further comprising a locking mechanism suitable for fastening the cartridge in place within the housing.

38. The device according to claim 19, wherein the cartridge is suitable for connection with an external drug source for supplying at least one drug to the internal organs.

39. The device of claim 19, further comprising at least one marking disposed on at least one of the cartridge and the housing that is suitable as an insertion direction indicator for the cartridge.

40. A body fluid cartridge exchange platform device, comprising:
a tubular cartridge insert,
a hollow tubular platform housing having a generally oval cross-section, a first end with a first opening and a second end with a second opening, wherein said first opening and said second opening facilitate insertion of said tubular cartridge insert that sealably engages inside the platform housing, and said first opening and said second opening facilitating bi-directional installation through either of said first opening and said second opening and bi-directional removal of said tubular cartridge insert through either of said first opening and said second opening regardless of which opening the tubular cartridge insert was installed through; and
a cartridge insert tool for executing a bi-directional cartridge insert installation and removal.

41. The device of claim 40, wherein the cartridge insert tool further comprises at least one marking disposed on at least the cartridge insert tool and the housing that is suitable as an insertion direction indicator for the tubular cartridge insert.

42. An access device for providing access to internal organs, comprising:
- a housing comprising having a first opening at a first end, a second opening at a second end, a first port disposed through a wall of the housing, a second port disposed through a wall of the housing, a first leg having at least a first passage in communication with the first port and a second leg having at least a second passage in communication with the second port, wherein the first leg extends in a staggered and divergent manner from the second extending leg along the wall of the housing; and
- a cartridge suitable for sealingly engaging an interior of the housing, the cartridge being insertable through either of the first opening and the second opening and removable through either of the first and second openings regardless of which opening the cartridge was inserted through.

43. An access device for providing access to internal organs, comprising:
- a housing having a first opening at a first end, a second opening at a second end a first leg having at least a first passage in communication with the first port and a second leg having at least a second passage in communication with the second port;
- a cartridge suitable for sealingly engaging an interior of the housing, the cartridge being insertable through either of the first opening and the second opening and removable through either of the first and second openings regardless of which opening the cartridge was inserted through, and
- a channel disposed within the cartridge that completes a flow path between the first passage and the second passage through the first and second ports and forming a first channel port and a second channel port at opposite ends of the channel within the cartridge, wherein a distance between the first channel port and a first end of the cartridge is greater than a diameter of the first channel port.

\* \* \* \* \*